US008924233B2

(12) United States Patent
Backhaus et al.

(10) Patent No.: US 8,924,233 B2
(45) Date of Patent: *Dec. 30, 2014

(54) ENHANCED MULTIPLE RESOURCE PLANNING AND FORECASTING

(75) Inventors: Brent Backhaus, Lakeville, MN (US); Lorna Backhaus, Lakeville, MN (US); Dean Ebesu, San Francisco, CA (US); Durand R. Van Arnem, Lakeville, MN (US)

(73) Assignee: Virtual Radiologic Corporation, Minneapolis, MN (US)

( * ) Notice: Subject to any disclaimer, the term of this patent is extended or adjusted under 35 U.S.C. 154(b) by 157 days.

This patent is subject to a terminal disclaimer.

(21) Appl. No.: 13/550,319

(22) Filed: Jul. 16, 2012

(65) Prior Publication Data

US 2013/0066646 A1    Mar. 14, 2013

Related U.S. Application Data

(63) Continuation of application No. 12/942,355, filed on Nov. 9, 2010, now Pat. No. 8,229,761, which is a (Continued)

(51) Int. Cl.
*G06Q 50/22* (2012.01)
*G06Q 10/06* (2012.01)
*G06Q 99/00* (2006.01)
*G06F 19/00* (2011.01)

(52) U.S. Cl.
CPC .............. *G06F 19/327* (2013.01); *G06Q 10/06* (2013.01); *G06Q 99/00* (2013.01); *G06Q 50/22* (2013.01)
USPC ............................................................ 705/2

(58) Field of Classification Search
USPC ............................................................. 705/2
See application file for complete search history.

(56) References Cited

U.S. PATENT DOCUMENTS 3,995,106 A    11/1976    Wern et al.
4,003,023 A    1/1977    Benson et al.
(Continued)

FOREIGN PATENT DOCUMENTS

WO    WO-01/99407 A1    12/2001
WO    WO-2005/006138 A2    1/2005
(Continued)

OTHER PUBLICATIONS

"24/7 Radiology Services", 24/7 Radiology, LLP, [online]. [retrieved on Nov. 2, 2006]. Retrieved from the Internet: <URL: http://www.247rad.comiservice.shtml>,/ (2004), 2 pgs.

(Continued)

*Primary Examiner* — John Pauls
(74) *Attorney, Agent, or Firm* — Schwegman Lundberg & Woessner, P.A.

(57) ABSTRACT

A system configuration and techniques for optimizing schedules and associated use predictions of a multiple resource planning workflow are disclosed herein, applicable to environments such as radiologist scheduling in a teleradiology workflow. In one embodiment, a series of computing engines and components are provided to allow detailed forecasting and the generation of customized recommendations for scheduling and other resource usage scenarios. This forecasting can factor resource efficiencies, changes in resource demand volume, resource specialties, resource usage preferences, expected future events such as the removal or addition of resources at future times, and other resource availability or usage changes. The forecasts may be further enhanced through the use of historical data models and estimated future data models. Additionally, a calendar and other tools may be presented through a user interface to allow forecast and scenario customization based on selection of a series of future dates.

21 Claims, 10 Drawing Sheets

Related U.S. Application Data continuation-in-part of application No. 12/783,073, filed on May 19, 2010, now Pat. No. 7,925,521, which is a continuation of application No. 11/288,645, filed on Nov. 28, 2005, now Pat. No. 7,729,928.

(60) Provisional application No. 60/656,215, filed on Feb. 25, 2005, provisional application No. 60/682,052, filed on May 17, 2005, provisional application No. 60/694,880, filed on Jun. 29, 2005, provisional application No. 60/699,119, filed on Jul. 14, 2005, provisional application No. 60/740,454, filed on Nov. 28, 2005, provisional application No. 60/740,589, filed on Nov. 28, 2005, provisional application No. 60/740,527, filed on Nov. 28, 2005.

(56) References Cited

U.S. PATENT DOCUMENTS

| | | | |
|---|---|---|---|
| 4,058,835 A | 11/1977 | Kennedy | |
| 4,261,018 A | 4/1981 | Knowlton | |
| 4,302,775 A | 11/1981 | Widergren et al. | |
| 4,458,267 A | 7/1984 | Dolazza | |
| 4,463,386 A | 7/1984 | Goddard et al. | |
| 4,541,012 A | 9/1985 | Tescher | |
| 4,604,653 A | 8/1986 | Shimizu | |
| 4,614,978 A | 9/1986 | Doster et al. | |
| 4,622,585 A | 11/1986 | Reitsma | |
| 4,631,521 A | 12/1986 | El-Sherbini | |
| 4,652,933 A | 3/1987 | Koshiishi | |
| 4,748,511 A | 5/1988 | Nicols et al. | |
| 4,764,870 A | 8/1988 | Haskin | |
| 4,860,112 A | 8/1989 | Nichols et al. | |
| 4,910,609 A | 3/1990 | Nicholas et al. | |
| 5,216,596 A | 6/1993 | Weinstein et al. | |
| 5,291,401 A | 3/1994 | Robinson | |
| 5,321,520 A | 6/1994 | Inga et al. | |
| 5,416,602 A | 5/1995 | Inga et al. | |
| 5,452,416 A | 9/1995 | Hilton et al. | |
| 5,469,353 A | 11/1995 | Pinsky et al. | |
| 5,469,535 A | 11/1995 | Jarvis et al. | |
| 5,513,101 A | 4/1996 | Pinsky et al. | |
| 5,631,953 A | 5/1997 | Thomas et al. | |
| 5,655,084 A | 8/1997 | Pinsky et al. | |
| 6,006,191 A | 12/1999 | DiRienzo | |
| 6,035,276 A | 3/2000 | Newman et al. | |
| 6,115,486 A | 9/2000 | Cantoni | |
| 6,137,527 A | 10/2000 | Abdel-Malek et al. | |
| 6,272,470 B1 | 8/2001 | Teshima | |
| 6,302,844 B1 | 10/2001 | Walker et al. | |
| 6,314,452 B1 | 11/2001 | Dekel et al. | |
| 6,381,029 B1 | 4/2002 | Tipirneni | |
| 6,424,996 B1 | 7/2002 | Killcommons et al. | |
| 6,448,956 B1 | 9/2002 | Berman et al. | |
| 6,473,524 B1 | 10/2002 | Reda et al. | |
| 6,481,887 B1 | 11/2002 | Mirabella | |
| 6,571,214 B2 | 5/2003 | Newman et al. | |
| 6,574,629 B1 | 6/2003 | Cooke, Jr. et al. | |
| 6,603,494 B1 | 8/2003 | Banks et al. | |
| 6,621,918 B1 | 9/2003 | Hu et al. | |
| 6,625,252 B2 | 9/2003 | Mirabella | |
| 6,678,703 B2 | 1/2004 | Rothschild et al. | |
| 6,798,533 B2 | 9/2004 | Tipirneni | |
| 6,820,057 B1 | 11/2004 | Loch et al. | |
| 6,876,759 B2 | 4/2005 | Keller et al. | |
| 6,915,266 B1 | 7/2005 | Saeed et al. | |
| 7,136,883 B2 | 11/2006 | Flamma et al. | |
| 7,500,185 B2 | 3/2009 | Hu | |
| 7,562,026 B2 | 7/2009 | DelMonego et al. | |
| 7,729,928 B2 | 6/2010 | Backhaus et al. | |
| 7,756,724 B2 | 7/2010 | Gropper et al. | |
| 7,925,521 B2 | 4/2011 | Backhaus et al. | |
| 7,970,634 B2 | 6/2011 | Backhaus et al. | |
| 8,090,593 B2 | 1/2012 | Backhaus et al. | |
| 8,145,503 B2 | 3/2012 | Backhaus et al. | |
| 8,195,481 B2 | 6/2012 | Backhaus | |
| 8,229,761 B2 | 7/2012 | Backhaus et al. | |
| 8,515,778 B2 | 8/2013 | Backhaus | |
| 8,612,250 B2 | 12/2013 | Backhaus et al. | |
| 8,612,253 B2 | 12/2013 | Backhaus et al. | |
| 2001/0032215 A1 | 10/2001 | Kyle et al. | |
| 2001/0041991 A1 | 11/2001 | Segal et al. | |
| 2002/0016718 A1 | 2/2002 | Rothschild et al. | |
| 2002/0019751 A1 | 2/2002 | Rothschild et al. | |
| 2002/0065758 A1 | 5/2002 | Henley | |
| 2002/0087503 A1 | 7/2002 | Judd et al. | |
| 2002/0102012 A1 | 8/2002 | Keller et al. | |
| 2002/0102028 A1 | 8/2002 | Keller et al. | |
| 2002/0109859 A1 | 8/2002 | Tipirneni | |
| 2002/0161605 A1 | 10/2002 | Newman et al. | |
| 2002/0169637 A1 | 11/2002 | Akers et al. | |
| 2002/0198454 A1 | 12/2002 | Seward et al. | |
| 2003/0004409 A1 | 1/2003 | Mueller et al. | |
| 2003/0061090 A1 | 3/2003 | Marano | |
| 2003/0086595 A1 | 5/2003 | Hu et al. | |
| 2003/0149598 A1 | 8/2003 | Santoso et al. | |
| 2004/0064343 A1 | 4/2004 | Korpman et al. | |
| 2004/0117617 A1 | 6/2004 | Geller et al. | |
| 2004/0167402 A1 | 8/2004 | Jones et al. | |
| 2004/0186764 A1 | 9/2004 | McNeill | |
| 2004/0254822 A1 | 12/2004 | Mandelbaum | |
| 2004/0257608 A1 | 12/2004 | Tipirneni | |
| 2005/0002483 A1 | 1/2005 | Wilcox, Jr. | |
| 2005/0021375 A1 | 1/2005 | Shimizu et al. | |
| 2005/0075902 A1 | 4/2005 | Wager et al. | |
| 2005/0101856 A1 | 5/2005 | Judd et al. | |
| 2005/0114380 A1 | 5/2005 | Eldar et al. | |
| 2005/0234741 A1 | 10/2005 | Rana et al. | |
| 2006/0053035 A1 | 3/2006 | Eisenberg | |
| 2006/0095423 A1 | 5/2006 | Reicher et al. | |
| 2006/0168338 A1 | 7/2006 | Bruegl et al. | |
| 2006/0195339 A1 | 8/2006 | Backhaus et al. | |
| 2007/0005798 A1 | 1/2007 | Gropper et al. | |
| 2007/0073556 A1 | 3/2007 | Lau et al. | |
| 2009/0089092 A1 | 4/2009 | Johnson et al. | |
| 2009/0198559 A1 | 8/2009 | Wang et al. | |
| 2009/0327049 A1 | 12/2009 | Kisin et al. | |
| 2010/0198609 A1 | 8/2010 | Mellin et al. | |
| 2010/0256986 A1 | 10/2010 | Backhaus et al. | |
| 2011/0004490 A1 | 1/2011 | Backhaus et al. | |
| 2011/0010192 A1 | 1/2011 | Backhaus et al. | |
| 2011/0015941 A1 | 1/2011 | Backhaus | |
| 2011/0066449 A1 | 3/2011 | Backhaus et al. | |
| 2011/0191118 A1 | 8/2011 | Backhaus et al. | |
| 2012/0245949 A1 | 9/2012 | Backhaus et al. | |
| 2012/0265551 A1 | 10/2012 | Backhaus et al. | |
| 2012/0323593 A1 | 12/2012 | Backhaus | |
| 2014/0088987 A1 | 3/2014 | Backhaus | |
| 2014/0142969 A1 | 5/2014 | Backhaus et al. | |
| 2014/0142983 A1 | 5/2014 | Backhaus et al. | |

FOREIGN PATENT DOCUMENTS

| | | |
|---|---|---|
| WO | WO-2006/093544 A3 | 9/2006 |
| WO | WO-2010/087911 A1 | 8/2010 |
| WO | WO-2012/064819 A1 | 5/2012 |

OTHER PUBLICATIONS

"About HL7", Health Level Seven, [online]. [retrieved on Jul. 15, 2005]. Retrieved from the Internet: <URL: www.hl7.org/about/about_nav_bar.cfm>, (2005), 15 pgs.

"About IHE", IHE Initiative: ACC/HIMSS/RSNA, [online]. [retrieved on Jul. 15, 2005]. Retrieved from the Internet: <URL: http://www.ihe.net/About/index.cfm>, (2005), 2 pgs.

"About Us!", Emergency Radiology, [Online]. [retrieved on Nov. 2, 2006]. Retrieved from the Internet: <URL: http://www.emergencyradiology.net/aboutus.htm> 1 pg.

"ACUO Technologies Products, ACUO Technology Product Webpage, Overview and Functionality data for (AcuoMed Image Manager & AcuoStore Digital Asses Manager)", ACUO Technologies, [Online]. [retrieved on Nov. 28, 2005]. Retrieved from the

(56) References Cited

OTHER PUBLICATIONS

Internet: <URL: http://www.acuotech.com/acuoArchive.html>, (2005), 5 pgs.

"ACUO Technology DICOM Archive", Acuo Technologies, LLC, [retrieved on Nov. 13, 2006]. Retrieved from the Internet: <URL: http://www.acuotech.com/acuoArchive.html>, 3 pgs.

"American Radiology offers Images Online to Referring Physicians", American Radiology Services, Inc, [online]. [archived on Feb. 23, 2005]. Retrieved from the Internet: <URL:http://www3.americanradiology.com/pls/web1/wwparticle.viewart?article_id_in=23>, (2003), 1 pg.

"American Radiology Services Nighthawk Services", © 2003 American Radiology Services, Inc., [online]. [retrieved Nov. 29, 2005]. Retrieved from the Internet: <URL: ]. http://www3.americanradiology.com/pls/web1/wwreadserv.info>, (2003), 2 pgs.

"American Radiology Services Organization Information", © 2003 American Radiology Services, [online]. [retrieved on Feb. 25, 2005]. Retrieved from the Internet: <URL: http://www3.americanradiology.com/pls/web1lwwaboutars.info >, (2003), 3 pgs.

"American Radiology Services, Inc.—Organization Information", © 2003 American Radiology, [online]. [retrieved on Feb. 25, 2005]. Retrieved from the Internet: <URL: http://www3.americanradiology.com/pls/web1/wwaboutars.info>, (2003), 3 pgs.

"APEX Radiology: A Virtual Radiologist on Staff", Apple Computer, Inc., [Online]. [retrieved Oct. 20, 2006]. Retrieved from the Internet: <URL: http://www.apple.com/science/profiles/apexl >, (2006), 4 pgs.

U.S. Appl. No. 11/288,645, Non Final Office Action mailed Nov. 12, 2009, 20 pgs.

U.S. Appl. No. 11/288,645, Notice of Allowance mailed Mar. 24, 2010, 12 pgs.

U.S. Appl. No. 11/288,645, Preliminary Amendment mailed Mar. 27, 2006, 4 pgs.

U.S. Appl. No. 11/288,645, Response filed Feb. 12, 2010 to Non Final Office Action mailed Nov. 12, 2009, 13 pgs.

U.S. Appl. No. 12/783,073, Notice of Allowance mailed Feb. 22, 2011, 9 pgs.

U.S. Appl. No. 12/783,073, Preliminary Amendment mailed Jan. 10, 2011, 7 pgs.

U.S. Appl. No. 12/856,096, Notice of Allowance mailed Jan. 25, 2012, 14 pgs.

U.S. Appl. No. 12/856,096, Response to Rule 312 Communication mailed Feb. 27, 2012, 2 pgs.

U.S. Appl. No. 12/870,271, Notice of Allowance mailed Feb. 24, 2012, 9 pgs.

U.S. Appl. No. 12/882,479, Notice of Allowance mailed Mar. 23, 2011, 11 pgs.

U.S. Appl. No. 12/882,479, Preliminary Amendment mailed Jan. 10, 2011, 10 pgs.

U.S. Appl. No. 12/942,355, Notice of Allowance mailed Apr. 12, 2012, 16 pgs.

U.S. Appl. No. 13/084,379, Notice of Allowance mailed Nov. 8, 2011, 13 pgs.

U.S. Appl. No. 90/009,889, Examiner Interview Summary mailed Jun. 28, 2011, 3 pgs.

U.S. Appl. No. 90/009,889, Notice of Failure to Comply mailed May 6, 2011, 8 pgs.

U.S. Appl. No. 90/009,889, Order mailed Jul. 13, 2011 Denying Request for ex parte Reexamination, 14 pgs.

U.S. Appl. No. 90/009,889, Petition for Reconsideration filed Aug. 10, 2011, 14 pgs.

U.S. Appl. No. 90/009,889, Revised Request for Re-Examination filed May 30, 2011, 10 pgs.

"Benefits", Fujifilm, [Online]. [retrieved on Nov. 28, 2005]. Retrieved from the Internet: <URL: www.fujifilm.co.uk/synapse/about/benefits>, (2004), 3 pgs.

"Cactus Advantage", Cactus Software, [online]. [retrieved on Nov. 2, 2006]. Retrieved from the Internet: <URL: http://www.visualcactus.com/Public2002/MCCACTUSAdvantageFull, (2006), 3 pgs.

"Cactus Software Products & Services", [online]. [retrieved on Nov. 2, 2006]. Retrieved from the Internet: <URL: http://www.visualcactus.com/Public2002/HomeFramedPage.htm>, (2006), 1 pg.

"California Radiographics Homepage", California Radiographics Inc., [online]. [retrieved on Sep. 7, 2005]. Retrieved from the Internet: <URL: http://www.nightshiftradiology.com/teleradiology_equipment.htm>, (2005), 4 pgs.

"Cascadable Architecture", © 2004 Fujifilm UK, [online], [retrieved on Nov. 28, 2005]. Retrieved from the Internet: <URL: www.fujifilm.co.uk/synapse/product/cascadable>, (2004), 2 pgs "Case Studies EchoApps", © 2006 Healthline Systems Inc., [online]. [retrieved on Nov. 2, 2006]. Retrieved from the Internet: <URL: http://www.healthlinesystems.com/casestudies/echoapps_mc.asp>, (2006), 5 pgs.

"Chatham Radiology Group Deploys Neurostar's Virtual Radiology Network Solution to Improve Service and Productivity", © 2003 Neurostar Solutions, [Online]. [retrieved on Apr. 26, 2005]. Retrieved from the Internet: <URL: www.neurostarsolutions.com/index/sp?page=PressRelease&newsID=2>, (2003), 3 pgs.

"Comply Product Overview", Strategic Management Group LLC, [Online]. [retrieved on Nov. 2, 2006]. Retrieved from the Internet: <URL: http://www.complysoftware.com/>, (2006), 2 pgs.

"Credentialing Software from Intellisoft", Intellisoft Group, Inc, [online]. [retrieved on Nov. 2, 2006]. Retrieved from the Internet: <URL: http://www.intellisoftgroup.com/>, 3 pgs.

"Database Management System", Fujifilm, [Online]. [retrieved on Nov. 28, 2005]. Retrieved from the Internet: <URL: www.fujifilm.co.uk/synapse/technical/database>, (2004), 1 pg.

"Desktop User Interface", 2004 Fujifilm UK, [Online]. [retrieved on Nov. 28, 2005]. Retrieved from the Internet: <URL: www.fujifilm.co.uk/synapse/product/desktop>, (2004), 2 pgs.

"Developing the Complete Teleradiology Infrastructure", The Hawk—The NightHawk Radiology Services Newsletter, (2005), 2 pgs.

"Diagna Radiology", [Online]. [retrieved on Feb. 25, 2005], Retrieved from the Internet: <URL: http://www.diagna.com/>, (2005), 12 pgs.

"Diagnosticimaging.com—Radiology is Going Places Let Us Take You There First", CMP Healthcare Media Group LLC, [Online]. [retrieved on Nov. 30, 2005]. Retrieved from the Internet: <URL: www.diagnosticimaging.com >, (2005), 4 pgs.

"DICOM Conformance Statement for Cedara I-SoftView", Cedara Software Corp, Document No. 2004-02987, (2005), 1-38.

"EchoApps", Healthline Systems Inc., [Online]. [retrieved on Sep. 6, 2005], Retrieved from the Internet: <URL: http://www.healthlinesystems.com/echoapps_mc.asp>, (2005), 3 pgs.

"EchoApps—Simplify the Provider Application Process", © 2004 HealthLine Systems Inc, [Online]. retrieved on Nov. 28, 2005]. Retrieved from the Internet: <URL: http://echomc.comlechoappsprocess2.asp>, (2004), 2 pgs.

"EchoApps Quick Tour, 12 Screen Captures", HealthLine Systems Inc., [online]. [retrieved on Nov. 28, 2005]. Retrieved from the Internet: <URL: http://healthlinesystems.com/demos/echoapps_demo.htm>, (2005), 13 pgs.

"EHR Clinical Overview", U.S. Department of Health and Human Services—Indian Health Service, [Online]. [retrieved on Jul. 15, 2005]. Retrieved from the Internet: <URL: http://www.ihs.gov/CIO/EHR/index.cfm?module=clinicaloverview>, (2005), 2 pgs.

"eMed—Test Drive Register", eMed® Technologies, [online]. [retrieved on Jul. 15, 2005]. Retrieved from the Internet: <URL: www.emed.com/products_services/matrix.php>, (2003), 4 pgs.

"Emergency Radiology Home Page", [online]. [retrieved on Nov. 12, 2006]. Retrieved from the Internet: <URL: http://www.emergencyradiology.net/missionstatement.htm>, 1 pg.

"Enterprise Image Management", GE Medical Systems, [Online]. [retrieved on Jul. 15, 2005] Retrieved from the Internet: <URL: www.gehealthcare.com/img_info_systems/centricity_ris/products/enterprise_img.html>, (2005), 2 pgs.

"Epic Teleradiology Services", © 2006 Epic Teleradiology, [Online]. [retrieved on Nov. 2, 2006]. Retrieved from the Internet: <URL: http://www.epictele.com/services.php>, (2006), 1 pg.

(56) References Cited

OTHER PUBLICATIONS

European Application Serial No. 94908280.4, Entscheidung, vol. 9, Board of Appeal of the European Patent Office, (Feb. 2005), 19 pgs.
European Application Serial No. 94908280.4, Office Action mailed Feb. 8, 2005, (2005), 19 pgs.
"Ex Parte Re-examination Request re: Backhaus et al., Patent No. 7,729,928 filed Dec. 17, 2010", 11 pgs.
"External Information System", © 2004 Fujifilm UK, [Online]. [retrieved Nov. 28, 2005]. Retrieved from the Internet: <URL: www.fujifilm.co.uk/synapse/technical/external>, (2004), 2 pgs.
"Fuji Receives Patent for Synapse's Subscription Technology", Fujifilm Medical Systems, [Online]. Retrieved from the Internet: <URL: http://www.fujimed.com/company-info/press-room/doc/press_subscription_technology.asp?location=3&area=25&id=0&subid=0, (2005), 2 pgs.
"Healthline Medical Imaging Modality Worklist DICOM Conformance Statement", Healthline Medical Imaging, (2005), 1-16.
"Healthline Medical Imaging Specification DICOM Conformance Statement", Healthline Medical Imaging, (2005), 27 pgs.
"HL7 Communications Module Definition Statement", Healthline Information Systems, Inc., (2005), 1-41.
"IDX® Imagecast tm Image Management—Radiology", [online]. © 1999-2005 IDX Systems Corporation. [retrieved Jul. 15, 2005]. Retrieved from the Internet: <URL: www.idx.com/imagecast/ic_im_rad.asp>, (2005), 3 pgs.
"IHE Cardiology Technical Framework Supplement 2005—Displayable Reports (DRPT)", ACC/HIMSS/RSNA, (2005), 1-41.
"IHE Organization", IHE initiative: ACC/HIMSS/RSNA, [online]. [retrieved on Nov. 30, 2005]. Retrieved from the Internet: <URL: http://www.ihe.net/About/Organization/org.cfm>, (2005), 3 pgs.
"Image Display Workstations", © 2O04 Fujifilm UK, [online]. [retrieved on Nov. 28, 2005]. Retrieved from the Internet: <URL: www.fujifilm.co.uk/synapse/technical/display>, (2004), 2 pgs.
"Images Acquisitions System", (c) 2004 Fujifilm UK, [online]. [retrieved Nov. 28, 2005]. Retrieved from the Internet: <URL: www.fujifilm.co.uk/synapse/technical/image>, (2004), 2 pgs.
"Images to any Desktop with Synapse", Fujifilm Medical Systems, Synapse Intelligent Connectivity, (2003), 2 pgs.
"Imaging on Call Is a JCAHO Accredited Facility", © 2005 Imaging on Call LLC, [Online], [retrieved on Nov. 3, 2006]. Retrieved from the Internet: <URL: http://www.imagingoncall.net/company/jcaho.php>, (2005), 1 pg.
"Integrated Web Technology", © 2004 Fujifilm UK, [Online]. [retrieved on Nov. 28, 2005] Retrieved from the Internet: <URL: : www.fujifilm.co.uk/synapse/product/webtechnology>, (2004), 2 pgs.
International Application Serial No. PCT/US05/43212, International Search Report mailed Sep. 26, 2007, 2 pgs.
International Application Serial No. PCT/US05/43212, Written Opinion mailed Sep. 26, 2007, 4 pgs.
International Application Serial No. PCT/US2011/059926, International Search Report mailed Mar. 1, 2012, 2 pgs.
International Application Serial No. PCT/US2011/059926, Written Opinion mailed Mar. 1, 2012 , 10 pgs.
"Medical Licensure Services", [online]. [retrieved on Sep. 7, 2005]. Retrieved from the Internet: <URL: http://www.medlicense.comlservoces.htrnl>, (2005), 3 pgs.
"MedModel—The Industry Standard for Healthcare Simulations", [Online]. [retrieved on Sep. 7, 2005] Retrieved from the Internet: <URL: http://www.promodel.com/products/medmodel>, (2005), 2 pgs.
"MedModel Simulation Plan your hospital and clinics using simulation software", Healthcare Planning Associates, [Online]. [retrieved on Nov. 29, 2005]. Retrieved from the Internet: <URL: : http://www.hpa.co.nz/index.asp?fpar=13732555342>, (2005), 2 pgs.
"Misys PACS Integration Module (PIM)", Misys Hospital Systems, Inc., [Online]. Retrieved from the Internet: <URL: http://www.misyshealthcare.com/NR/rdonlyres/11B3E4E4-B08B-4A78-970E-D37B8B69CCBF/0/misysPIMrev4.pdf#search=%22Misys%20PACS%20Integration%20Module%20(PIM)%22>, (2004), 2 pgs.

"Mobile Imaging", Empire Teleradiology Associates, LLC, [Online]. Retrieved from the Internet: <URL: http://www.empiretelerad.com/emp_mobile.htm>, (2002), 1 pg.
"Multi-Site PACS with Synapse", © 2003 Fujifilm Medical Systems, Synapse Intelligent Connectivity, (2003), 2 pgs.
"National Practitioner Data Bank Healthcare Integrity and Protection Data Bank", NPDB-HIPDB, [online]. [retrieved on Jul. 18, 2005]. Retrieved from the Internet: <URL: http://www.npdb-hipdb.com/npdb.html>, (2005), 3 pgs.
"Network", © 2004 Fujifilm UK, [online].]. [retrieved on Nov. 28, 2005]. Retrieved from the Internet: <URL: www.fujifilm.co.uk/synapse/technicaVnetwork>, (2004), 2 pgs.
"Night and Weekend Call Service", © RadLinx Group, [online]. [retrieved on Nov. 29, 2005]. Retrieved from the Internet: <URL: : http://www.radlinxgroup.com/nighthawk.html>, (2005), 3 pgs.
"Night Shift Radiology", Schematic of NightShift Radiology Network, NightShift Radiology, [Online]. [retrieved on Nov. 28, 2005]. Retrieved from the Internet: <URL: http://www.nightshiftradiology.coml network.htm>, 2 pgs.
"Nighthawk Pros Premier Night-Time Coverage—NightHawk Pros Company Profile, Teleradiology Overview of Services, Teleradiology Solutions for Radiology Experts, Teleradiology Technology Solutions", Nighthawk Pros, [Online]. Retrieved from the Internet: <URL: http://www.nighthawkpros.com/>, (2005), 4 pgs.
"Nighthawk Radiology Services Contact Information—contact information, company information, services, network technology", Nighthawk Radiology Services, [Online]. [retrieved on Feb. 25, 2005]. Retrieved from the Internet: <URL: http://www.nighthawkrad.net/>, (2005), 5 pgs.
"NightRays credentialing", NightRays, [Online], Retrieved from the Internet: <URL: http://www.nightrays.comlcredreq.pdf>, (published before Mar. 7, 2007), 1 pg.
"NightShift Radiology—Overview", NightShift Radiology, [online]. [retrieved on Feb. 2, 2005]. Retrieved from the Internet: <URL: http://www.nightshiftradiology.com/., (2005), 3 pgs.
"NightShift Radiology Preliminary Report, Sample Report", Nightshift Radiology, [Online]. [retrieved on Feb. 25, 2005]. Retrieved from the Internet: <URL: http://www.nightshiftradiology.com/sample_report.htm>, (2001), 6 pgs.
"Nightshift Radiology: Our Network Built for Reliability", Nightshift Radiology, [online]. [retrieved Nov. 28, 2005]. Retrieved from the Internet: <URL: http://www.nightshiftradiology.com/network.htm>, (2005), 2 pgs.
"Non-Emergency Solve the Demand for Radiologists", © 2006 Diagna Radiology, [Online]. [retrieved Nov. 3, 2006]. Retrieved from the Internet: <URL: www.diagna.com/nonemerg.htm>, (2006), 2 pgs.
"On Demand Access to data", Fujifilm, [Online]. Retrieved from the Internet: <URL: www.fujifilm.co.uk/synapse/product/ondemand>, (2004), 2 pgs.
"OneApp Credentialing Software", © 2005 SyMed Development, Inc., [Online]. [retrieved on Sep. 7, 2005]. Retrieved from the Internet: <URL: : http://www.symed.comlproducts/oneapp>, 2 pgs.
"OneApp Product Tour", SyMed, [Online]. [retrieved on Nov. 28, 2005]. Retrieved from the Internet: <URL: http://www.symed.comlproducts/oneapptour-l.asp>, (2005), 6 pgs.
"Partners you can trust", International Teleradiology Corporation, [Online]. Retrieved from the Internet: <URL: http://www.teleradiologyonline.comlindex.htm >, (2006), 1 pg.
"Product Data AON Tool Set Software Release Version 3.0", Fujifilm Medical Systems, (2003), 2 pgs.
"Product Data Server Software Release Version 3.0", Fujifilm Medical Systems, Synapse Intelligent Connectivity, (2003), 2 pgs.
"Project Title: Developing a Prototype for a Nationwide Health Information Network Architecture", Request for Proposal (RFP) ONCHIT-3, Section C—Descriptions/Specifications/Work Statement, (2010), 9 pgs.
"Proscan Reading Services™—World Leaders in Medical Imaging Interpretation", Proscan Reading Services, [Online]. Retrieved from the Internet: <URL: http://www.proscan.comlfw/mainlfw_link.asp?URL=/_filelib/FileCabinet/PDFIProScanReadingService.pdfOlo3FFileName%3DProScanReadingService.pdf&Titie=Reading%20Services%20 Brochure>, (before Mar. 7, 2007), 9 pgs.

(56) References Cited

OTHER PUBLICATIONS

"Radiology PACS RadWorks 5.0 Standard", Wipro GE Healthcare, [online]. [retrieved on Jul. 15, 2005]. Retrieved from the Internet: <URL: www.gehealthcare.com/inen/it_solutions/rad_pacs/ products/rad/msiisrwst2.html.html>. 3 pgs.

"Radiology PACS RadWorks 5,1 Standard", Wipro GE Healthcare, [Online]. [retrieved on Jul. 15, 2005], Retrieved from the Internet: <URL: www.gehealthcare.comlineniitsolutions/radpacs/products/ radlradworks.html>, (2005), 2 pgs.

"Rapid Reliable Radiology Technology", StatRad, [Online]. Retrieved from the Internet: <URL: http://statrad.comltechnology. html>, (published before Mar. 7, 2007), 2 pgs.

"Rapid Response Radiology tm", Consulting Radiologists, Ltd, [online]. [retrieved on Nov. 3, 2006]. Retrieved from the Internet: <URL: http://www.consultingradiologists.comlrapidresponse technology.htm >, (2006), 1 pg.

"RIS Radiology Information System Online Data Entry for Nighttime Teleradiology Studies", Virtual Radiologic Consultants, Startup Guide v1.7,, (May 16, 2005), 19 pgs.

"RSI Difference", (published prior to Nov. 10, 2010), 3 pgs.

"Santa Barbara County Care Data Exchange", [Online]. Retrieved from the Internet: <URL: http://www.chcf.org/documents/ ihealthJSantaBarbaraFSWeb.pdf.>, (2007), 4 pgs.

"SkyRIS TeleRIS—Complete workftow, reporting and distribution solution for multi-contract radiology and teleradiology", ThinAir Data, (2004), 2 pgs.

"SkyRISE Enterprise—Enterprise speech recognition interfaced to existing HIS/RIS", ThinAir Data, (2004), 2 pgs.

"Software Solutions for Today's Healthcare Professionals", © 2006 Morrisey Associates, [online]. [retrieved on Nov. 3, 2006]. Retrieved from the Internet: <URL:.http://www.morriseyonline.coml >, (2006), 1 pg.

"Special Report: What's all the noise about tele-radiology?", RadLinx Group, [Online], Retrieved from the Internet: <URL: http:// www.radlinxgroup.comlarticie noise teleradiology.html>, 3 pgs.

"StatRAD—Rapid, Reliable Radiology", Welcome, About Us, Services, Jobs, Contact Stat Radiology, [Online]. [retrieved on Feb. 25, 2005]. Retrieved from the Internet: <URL: http://statrad.comlindex. html>, (2005), 9 pgs.

"Storage System", © 2004 Fujifilm UK, [Online] [retrieved on Nov. 28, 2005]. Retrieved from the Internet: <URL: www.fujifilm.co. ukJsynapse/technicaVstorage>, (2004), 2 pgs.

"Sy Med Simplifying Managed Care", Sy.Med Development, Inc, [Online]. Retrieved from the Internet: <URL: http://www.symed. coml>. 1 pg.

"Synapse User's Manual Quick Reference Guide", Fujifilm Medical Systems, Software Version 3.0.0,2002, Fulifilm Medical Systems, (2002), 198 pgs.

"Synapse Version 3.0.0 Systems Administration Manual", Fujifilm, (2003), 1-55 pgs.

"Synapse™ Version 3.0.0 Workstation Administration Manual", Fujifilm, (2004), 1-62.

"TDS Network Welcome", Teleradiology Diagnostic Service, [Online], Retrieved from the Internet: <URL: http://www. tdsnetwork.neti>, (2004), 2 pgs.

"Technical Features", Fujifilm, [Online]. Retrieved from the Internet: <URL: www.fujifilm.co.uk/synapse/technical>, (2004), 2 pgs.

"Technically, It's Important", © 2006 TeamHealth Radiology, [Online]. Retrieved from the Internet: <URL: http://www. thteleradiology.comltechnology.htrn>, (2006), 3 pgs.

"Teleradiology Solutions about us, services, contact us", Teleradiology Solutions, [Online]. [retrieved on Feb. 25, 2005]. Retrieved from the Internet: <URL: ttp://www.telradsol.coml>, (2005), 4 pgs.

"Teleradiology: At Work Night and Day", Harris, [Online]. ]. [retrieved on Nov. 3, 2006]. Retrieved from the Internet: <URL: www.healthimaging.com/content/view/479/681>, (2006), 5 pgs.

"TeleShare", Dejarnette Research Systems, [Online]. Retrieved from the Internet: <URL: http://www.dejarnette.comll024/requestedpage. asp?Content=Products/>, (2004), 2 pgs.

"Templeton Radiology", Templeton Readings LLC, [Online]. Retrieved from the Internet: <URL: http://www.templetomadiology. com>, (2004), 9 pgs.

"Templeton Radiology Night Solutions", © 2004 Templeton Radiology, [Online]. [retrieved on Nov. 29, 2005]. Retrieved from the Internet: <URL: http://www.templetomadiology.com/night_so1. htrn>, (2004), 2 pgs.

"Templeton Radiology Physician Credentialing", Templeton Radiology, [Online]. [retrieved on Sep. 7, 2005], Retrieved from the Internet: <URL: : http://www.templetomadiology.comlpc.htrn>, 2 pgs.

"Templeton Radiology Radiology Services", Templeton Radiology, [online]. [retrieved on Nov. 29, 2005]. Retrieved from the Internet: <URL: http://www.idshealthcare.com/hospital_management/global/templeton_radiology/web_enabled dictation! .. >, (2005), 3 pgs.

"Templeton Radiology RISIPACS website product information", © 2004 Templeton Radiology, [online]. [retrieved on Nov. 29, 2005]. Retrieved from the Internet: <URL: http://www.templetomadiology. comlpacs.htrn>, (2004), 2 pgs.

"Templeton Radiology RISIPACSIWEB/ARCHIVE managed solution", Templeton Radiology, [online]. [retrieved on Nov. 29, 2005]. Retrieved from the Internet: <URL: http://www.templetomadiology. comlpacs.htrn>, (2005), 6 pgs.

"Templeton Radiology Teleradiology Night Solutions", Templeton Radiology, [online]. [retrieved on Nov. 29, 2005). Retrieved from the Internet: <URL: http://www.idshealthcare.com/hospitat management/global/templeton radiology/ templeton_mobile readings/. htrn>, (2005), 3 pgs.

"The Project", GlobalRad® Non-Profit Foundation, [online]. [retrieved on Nov. 3, 2006]. Retrieved from the Internet: <URL: http://www.globalrad.org/project.htrn>, (2006), 1 pg.

"The RadLinx Group Ltd,—FAQ's"; [online]. [retrieved on Nov. 29, 2005]. Retrieved from the Internet: <URL: http://www.radlinxgroup. com/faq.html>, (2005), 2 pgs.

"The Work Flow Process", Imaging on Call, LLC, [Online], ]. [retrieved on Nov. 3, 2006]. Retrieved from the Internet: <URL: http://www.imagingoncall.net/technology/sat.php>, (2006), 1 pg.

"ThinAir Data—Healthcare at the Speed of Thought", [online]. [archived on Nov. 11, 2004]. Retrieved from the Internet: <URL: http://web.archive.org/ web/20041112045011/ http://www. thinairdata.com>, (2004), 2 pgs.

"U.S. Based Client Services", © RadLinx Group, [online]. [retrieved on Nov. 29, 2005]. Retrieved from the Internet: <URL: http://www. radlinxgroup.comlc1ient.html>, (2005), 2 pgs.

"US Radiology On-Call—Locations, Services, Technology, Radiologists, FAQ, Contact Us", [Online]. [retrieved on Feb. 25, 2005]. Retrieved from the Internet: <URL: http://www.usroc.com/>, (2005), 7 pgs.

"US Radiology On-Call FAQ", US Radiology On-Call, [online]. [retrieved on Nov. 3, 2006]. Retrieved from the Internet: <URL: http://www.usroc.comlfaq.htrnl >, (2006), 2 pgs.

"US Radiology On-Call Radiologists", © US Radiology On-Call, [online]. [retrieved on Nov. 3, 2006]. Retrieved from the Internet: <URL: http://www.usroc.comlradiologists.htrnl>, (2006), 1 pg.

"US Radiology On-Call-Locations, Services, Technology, Radiologists, FAQ, Contact Us", US Radiology, [online]. [retrieved on Feb. 25, 2005]. Retrieved from the Internet: <URL: http://www.usroc. coml >, (2005), 7 pgs.

"Veritas Product data (V-Form)", Veritas Medical Services, Inc. [online]. [retrieved on Sep. 7, 2005], Retrieved from the Internet: <URL: http://www.veritasmed.comlproducts/>, (2005), 3 pgs.

"Virtual Radiologic™ Physician Services Operating Manual", Virtual Radiologic Consultants, Inc., (2005), 75 pgs.

"Vistar Technologies—Automated Credentialing Software CVOs and Medical Societies", © 2005 Vistar Technologies, [online]. [retrieved on Nov. 3, 2006]. Retrieved from the Internet: <URL: http://vistartech.comlcvomed.htm >, (2005), 1 pg.

"Visual Cactus", Cactus Software, [Online]. Retrieved from the Internet: <URL: http://www.visualcactus.comlPublic2002/images/ HospitalFlyer-2005.pdf.>,, (2005), 1 pg.

"VRN—A Step Beyond Teleradiology", © 2005 NeuroStar Solutions, [online]. [retrieved on Nov. 30, 2005]. Retrieved from the Internet: <URL: http://www.neurostarsolutions.com/cms/theVRN/ vrnApplicationServices/pacs.html, (2005), 2 pgs.

"Welcome to MedTel International", MedTel International, [online]. [retrieved on Nov. 3, 2006]. Retrieved from the Internet: <URL: http://www.medtel.coml >, (2006), 1 pg.

(56) References Cited

OTHER PUBLICATIONS

"Why the NPDB Was Created", National Practioner Data Bank, [Online]. [retrieved on Nov. 30, 2005]. Retrieved from the Internet: <URL: http://www.npdb-hipdb.comlnpdb.htrnl>, (2005), 2 pgs.
"WIN/Staff PRO-FILE", WIN/Staff, [Online]. Retrieved from the Internet: <URL: http://www.winstaff.comlmarketing/prac J>ro file. htrn >, (2002), 1 pg.
"World Wide Rad FAQ", World Wide Rad [online]. [retrieved on Nov. 3, 2006]., Retrieved from the Internet: <URL: http://www.worldwiderad.comlWWRWebsite files/frame.htm >, (2006), 1 pg.
Batchelor, J. S., "Remote-controlled MRI tackles tech shortage", [Online]. Retrieved from the Internet: <URL: http://www.auntminnie.comlindex.asp?sec=ser&sub=def&pag=dis&ItemID=69371>, (2006), 2 pgs.
Brice, J. "Continued IT evolution boosts teleradiology", NightHawk Radiology Services, (Feb. 2004), 5 pgs.
Collins, J. E., et al., "Automated Assignment and Scheduling of Service Personnel", *IEEE Expert*, (Apr. 1994), 33-39.
Finarelli, H. J., et al., "Effective demand forecasting in 9 steps Shifts in demand for a hospital's services can occur unexpectedly. Demand forecasting can help you prepare for these shifts and avoid strategic missteps", Retrieved from Internet: http://findarticles.com/p/articles/mi_m3257/is_11_58/ai_n635908/, (Nov. 2004), 13 pgs.
Harrell, C. R., et al., "Healthcare Simulation Modeling and Optimization using MedModel", *Proceedings of the 2000 Winter Simulation Conference*, Joines et al., eds., (2000), 203-207.
Khan, R. N., *Business Process Management: A Practical Guide*, (Sep. 2004), 103-124.
Khan, R. N., *Business Process Management: A Practical Guide*, (Sep. 2004), p. 179.
Khan, R. N., *Business Process Management: A Practical Guide*, (Sep. 2004), 207-222.
Khan, R. N., "Smart Ways of Routing Work, Business Process Management: A Practical Guide", [Online]. Retrieved from the Internet: <URL: http://www.bpm.com/smart-ways-of-routing-work.html>, (Sep. 2004), 4 pgs.
May, T., "Home work may solve doc shortage", [Online]. [retrieved on Jan. 22, 2007]. Retrieved from the Internet: <URL: www.usrp.net/articles/Home work.htrnl>, (2007), 2 pgs.
Osborne, J. W., et al., "The Power of Outliers(and why researchers should Always check for them)", *Practical Assessment, Research & Evaluation*, 9(6), (Nov. 2004), 28 pgs.
Page, D., "To the ends of the Earth", Diagnostic Imaging, [Online]. Retrieved from the Internet: <URL: www.diagnosticimaging.comlspecialedition2003l?page=teleradiology.htrnl >, (2003), 7 pgs.
Skyris, "Full feature RIS with integrated speech recognition and transcription", ThinAir Data, (2004), 2 pgs.
Thinair Data, Skyris Teleradiology, "TeleRIS is the complete teleradiology, multi-contract, multi-facility workftow, reporting and distribution solution", [Online]. Retrieved from the Internet: <URL: http://web.archive.org/web/20050204055213/www.thinairdata.com/SkyRISTele.htm, (2005), 3 pgs.
U.S. Appl. No. 13/333,767, Notice of Allowance mailed Aug. 22, 2013, 12 pgs.
U.S. Appl. No. 13/423,513, Notice of Allowance mailed Aug. 20, 2013, 11 pgs.
U.S. Appl. No. 13/423,513, Supplemental Notice of Allowability mailed Oct. 10, 2013, 5 pgs.
Canadian Application Serial No. 2,636,705, Office Action mailed Mar. 12, 2014, 3 pgs.
"Defendants' Supplemental Prior Art Statement dated Apr. 11, 2014", *Virtual Radiologic Corporation, et al. v. Tandem Radiology, LLC, et al.*, (Civil Action No. 2:13-cv-01705-DKD, United States District Court for the District of Arizona), 27 pgs.
"Ex. A—Invalidity Chart of U.S. Patent No. 8,195,481", (Apr. 11, 2014), 140 pgs.
"Ex. B—Invalidity Chart of U.S. Patent No. 7,970,634", (Apr. 11, 2014), 182 pgs.
"Ex. C—Invalidity Chart of U.S. Patent No. 8,145,503", (Apr. 11, 2014), 285 pgs.
"Ex. D—Invalidity Chart of U.S. Patent No. 8,090.593", (Apr. 11, 2014), 132 pgs.
"Ex. E—Invalidity Chart of U.S. Patent No. 8,515,778", (Apr. 11, 2014), 115 pgs.
"MGRIS—Global Radiology Information System", Medweb®, (before Nov. 2013), 1 pg.
"RIS Logic Module Workflow Functionality Highlights", [online]. [archived on Jan. 5, 2004]. Retrieved from the Internet: <URL: http://web.archive.org/web/20040105160056/ http://www.merge.com/products/pacsteleradiologyweb/rislogiccs_features.asp>, (2004), 6 pgs.
"State Telemedicine Licensure as of Jul. 15, 2001", [online]. © 1994-2002 American College of Radiology. [archived on Sep. 17, 2002]. Retrieved from the Internet: <URL: http://web.archive.org/web/20020917202928/http://www.acr.org/cgi-bin/fr?mast:mastheaddepartments,text:/departments/govt_rel/text.html>, (Revised Feb. 2002), 7 pgs.
"ThinAir Data", Promotional Material, (before Nov. 2013), 2 pgs.
"ThinAir Data—SkyRIS DR—Bringing Speech, Wireless & Internet Technologies to Healthcare", [online]. [archived on Jun. 7, 2001]. Retrieved from the Internet: <URL: http://web.archive.org/web/20010607094324/http://thinairdata.com/SkyRIS/DR/dr.html>, (2001), 1 pg.
"ThinAir Data—SkyRIS—Speech, Wireless and the Internet—Healthcare at the speed of thought", (before Nov. 2013), 2 pgs.
"ThinAir Data—SkyRIS Teleradiology—Speech, Wireless and the Internet—Healthcare at the speed of thought", (before Nov. 2013), 2 pgs.
"ThinAir Data—SkyRIS TeleRIS—Speech, Wireless and the Internet—Healthcare at the speed of thought", (before Nov. 2013), 2 pgs.
Berger, S. B., et al., "Medical-Legal Issues in Teleradiology", *AJR*, 166, (1996), 505-510.
Brice, James, "Globalization comes to radiology", [online]. © 1996-2004 CMP Media LLC. [retrieved on May 22, 2014]. Retrieved from the Internet: <URL: http://web.mit.edu/outsourcing/class1/DI-radiology-1.htm>, (Nov. 2003), 7 pgs.
Chacko, Anna K., et al., "Vision and benefits of a virtual radiology environment for the U.S. Army", (Abstract), *Proc. SPIE 3339, Medical Imaging 1998: PACS Design and Evaluation: Engineering and Clinical Issues*, 200, (1998), 2 pgs.
Kalyanpur, Arjun, et al., "Implementation of an International Teleradiology Staffing Model", *Radiology*, 232(2), (Aug. 2004), 415-419.
Martinez, Ralph, et al., "Virtual Management of Radiology Examinations in the Virtual Radiology Environment Using Common Object Request Broker Architecture Services", *Journal of Digital Imaging*, 12(2)(Suppl. 1), (1999), 181-185.
Mun, Seong G., et al., "Teleradiology and emerging business models", *J. Telemed. Telecare*, 11(6), (2005), 271-275.
Siegel, Eliot, et al., "Work Flow Redesign: The Key to Success When Using PACS", *AJR*, 178, (Mar. 2002), 563-566.
U.S. Appl. No. 13/333,767, Non Final Office Action mailed Mar. 20, 2013, 18 pgs.
U.S. Appl. No. 13/333,767, Response filed Jul. 18, 2013 to Non Final Office Action mailed Mar. 20, 2013, 15 pgs.
U.S. Appl. No. 13/423,513, Non Final Office Action mailed Mar. 19, 2013, 16 pgs.
U.S. Appl. No. 13/423,513, Response filed Jul. 18, 2013 to Non Final Office Action mailed Mar. 19, 2013, 16 pgs.
U.S. Appl. No. 13/449,004, Notice of Allowance mailed Apr. 22, 2013, 13 pgs.
U.S. Appl. No. 90/009,889, Reexamination Petition Decision mailed Aug. 1, 2012, 15 pgs.
International Application Serial No. PCT/US2011/059926, International Preliminary Report on Patentability mailed May 23, 2013. 12 pgs.

ENHANCED MULTIPLE RESOURCE PLANNING AND FORECASTING

CROSS REFERENCE TO RELATED CASES

This application is a continuation application of prior U.S. patent application Ser. No. 12/942,355 filed Nov. 9, 2010 and entitled "Enhanced Multiple Resource Planning and Forecasting", which is a continuation-in-part of prior U.S. patent application Ser. No. 12/783,073 filed May 19, 2010 and entitled "Multiple Resource Planning System", which is a continuation of prior U.S. patent application Ser. No. 11/288,645 filed Nov. 28, 2005 and entitled "Multiple Resource Planning System", which claims the benefit of U.S. Provisional Patent Application Nos. 60/656,215, filed Feb. 25, 2005 by Backhaus and entitled "Automated Credentialing and Licensing System"; 60/682,052, filed May 17, 2005, by Backhaus et al. and entitled "Integrated Caching Environment with Order Form Pre-population"; 60/694,880, filed Jun. 29, 2005, by Backhaus et al., and entitled "Medical Data Management Method and System"; 60/699,119, filed Jul. 14, 2005, by Backhaus et al., and entitled "Medical Data Transfer System and Method"; 60/740,454, filed Nov. 28, 2005 by Backhaus et al., and entitled "Medical Data Transfer System and Method"; 60/740,589, filed Nov. 28, 2005 by Casey et al. and entitled "Remote Scanning System and Method"; and 60/740,527, filed Nov. 28, 2005 by Casey et al. and entitled "Patient Information Translation Method and System"; the entirety of all of the preceding applications are incorporated herein by reference.

FIELD OF THE INVENTION

The present invention generally relates to medical image data processing and the evaluation of radiological images. The present invention more specifically relates to enhanced planning and forecasting strategies that more accurately predict future usage and resource requirements in connection with radiology processing and evaluation services.

BACKGROUND OF THE INVENTION

Medical images, such as X-rays, CAT (computerized axial tomography) scans, and MRI's (Magnetic Resonance Imaging), may be digitized to facilitate reading by doctors at remote locations. Hospitals and other healthcare providers commonly use electronic systems to capture and digitize the medical images. The medical images are typically transmitted from the modality to a remote image server such as a Picture Archiving and Communications System (PACS). This transmission may occur over a network, such as an intranet or the Internet.

Additionally, the hospital may also transmit orders corresponding to the images to an order server, such as a Radiologist Information System (RIS). The orders may be requests for a doctor to interpret, or read, the images and return a diagnostic report. Orders may also contain information, such as a patient identifier, the procedure type associated with the image, patient demographic information, and a hospital identifier. Thus, orders may be submitted by hospitals and healthcare providers to identify the patient and instruct the radiologist to provide information for a specific medical condition.

Existing PACS and RIS systems are generally not configured to facilitate the type of workflow activities that occur in remote radiological reads, and therefore these systems cannot adequately plan for their usage. The need for radiological scans and remote radiological reads, particularly in off-peak (nights, weekends, and holidays) and emergency-driven settings, will vary significantly.

As a further complexity, only certain radiologists may be able to read individual studies. For example, a radiologist with a specialty of neurology is best suited to read radiology images of the brain. And even if the radiologist is medically qualified, the radiologist will need to be properly credentialed with the requesting medical facility (e.g., being granted privileges to practice in the medical facility) and licensed in the jurisdiction of the medical facility (e.g., being licensed by a State Board of Radiology where the hospital resides). Based on the large number of variables involved in selecting the appropriate radiologist for reads, it is particularly challenging for a radiology provider to accurately estimate staffing needs. Enhanced techniques are needed to improve the forecasting and prediction of usage for radiological image reads, particularly for radiology studies provided in connection with a teleradiology workflow.

BRIEF SUMMARY OF THE INVENTION

One aspect of the present invention disclosed herein relates to enhanced planning and forecasting strategies which provide usable data for a radiology read workflow. In a workflow where a request such as a radiology study is assigned to a selected resource (such as a radiologist selected from a pool of potential radiologists), the volume of the requests and the timing of the request must be accurately predicted to ensure adequate resources (i.e., radiologist staffing levels) and prevent service outages.

In a specific embodiment described herein, a technique for forecasting radiology read demand and radiologist staffing within a future time period includes factoring both historical demand information and future demand information to forecast a probability and timing of the changes to radiologist availability and radiology read request volume expected to occur prior to or during the future period of time. This historical demand information may include historical data values of radiology read requests that were recorded during a past period of time, with the past period of time having one or more equivalent characteristics to the future period of time. The future demand information may include changes to radiologist availability and radiology read request volume expected to occur prior to or during the future period of time.

To perform the forecast, expected radiology read request volume is compared with expected radiologist availability for the future period of time to determine any shortfall or excess in staffing levels. Expected radiologist availability for the future period of time is calculated by factoring the forecasted probability and timing of the changes to radiologist availability, and expected radiology read request volume for the future period of time is calculated by modifying the historical data values with the forecasted probability and timing of the changes to radiology read request volume.

In another specific embodiment disclosed herein, the planning and forecasting technique includes processing baseline data and extrapolating the baseline data to a future time period. The baseline data is obtained from radiology read activities performed for a set of past medical facilities which have common characteristics to a set of future medical facilities projected for the future time period. Once radiology staffing and demand changes are estimated for the future time period, the changes may be integrated into the baseline data with use of a data model. From this data model, expected radiology read demand at the future set of medical facilities may be generated for the future time period.

Other specific embodiments include a system configured for implementing enhanced planning and forecasting strategies for multiple resource planning in a teleradiology workflow in accordance with the techniques described herein; and a computer program product configured for implementing enhanced planning and forecasting strategies for multiple resource planning in a teleradiology workflow, with the computer program product comprising a computer readable storage medium having computer readable code embodied therewith, each of these computer program products executable on computing hardware and machines to implement the techniques described herein.

BRIEF DESCRIPTION OF THE DRAWINGS

Like reference symbols in the various drawings indicate like elements.

DETAILED DESCRIPTION OF THE INVENTION

One aspect of the disclosed invention relates to enhanced techniques for modeling and optimizing the availability of one or more resources. These techniques are particularly applicable for a finite set of resources whose usage must be forecasted and modeled. For example, in a teleradiology setting as described herein, an adequate number radiologists who are eligible to perform the requested radiology reads must be available. Failure to predict the number of radiologists required and factor which radiologist can perform reads for the various medical conditions or medical facilities encountered may lead to delays or service outages. The following description of remote radiology practices will illustrate the need for the enhanced forecasting and prediction techniques of the present invention in detail.

Figure 1A:
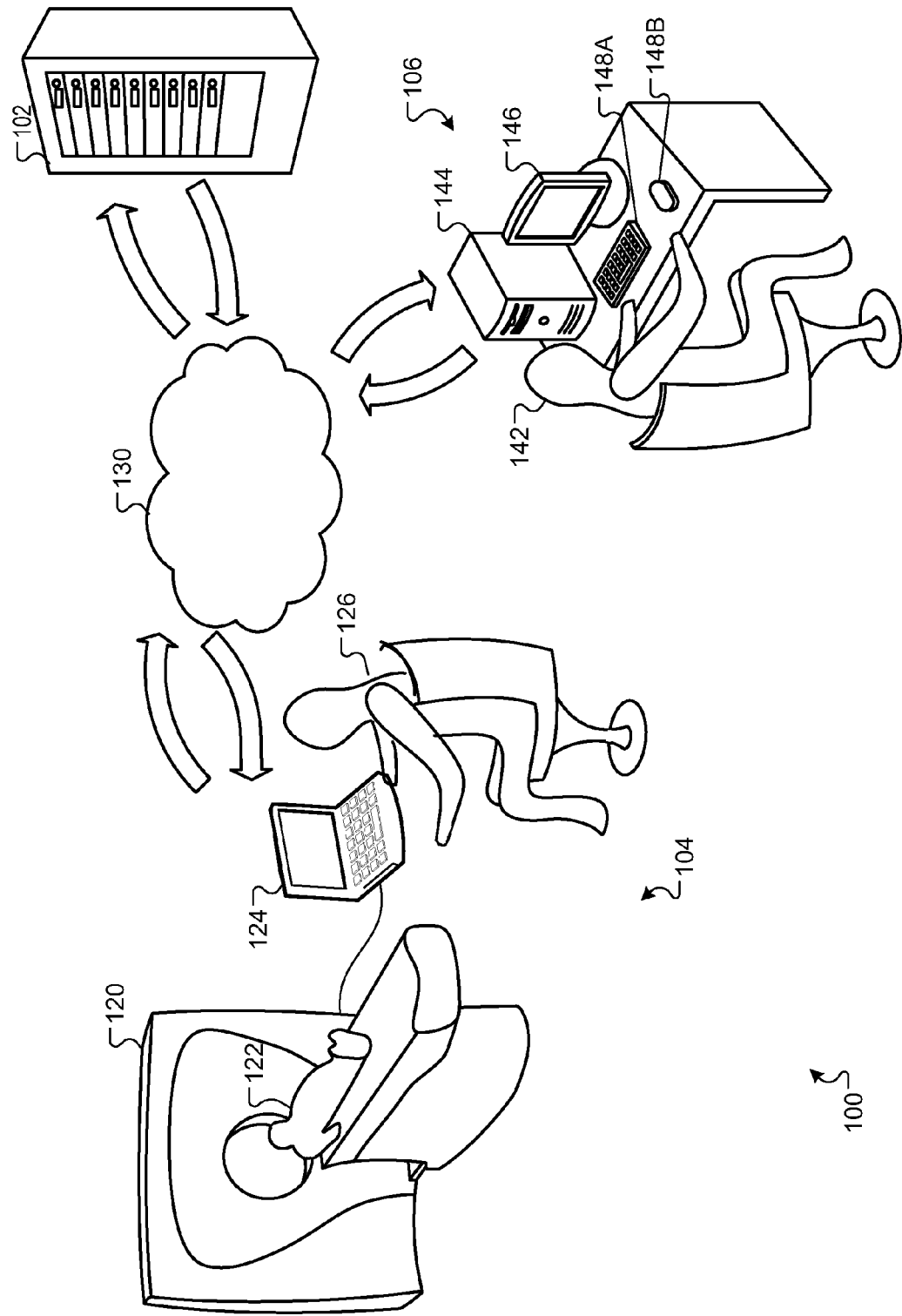
FIG. 1A is an illustration of a radiology system configured for assigning radiology study medical requests to remote doctor systems.

Referring to FIG. 1A, operation of an example radiology system 100 configured for assigning radiology study medical requests to remote doctor systems is illustrated. The system 100 can be used for capturing medical image data in one location and for reviewing medical images associated with the data in another location. The system 100 may include many geographically separated imaging devices and many image review terminals. Therefore, system 100 might be configured to operate as a remote teleradiology system connected to a plurality of healthcare locations, or as a localized radiology system used in a single hospital, healthcare provider network, or private radiology practice.

For purposes of illustration, the radiology system 100 illustrated in FIG. 1A includes an imaging system 104, an image order (IO) management system 102, and an image review system 106. The imaging system 104, for example, may include an imaging device 120, such as a CT (computer tomography) scanner, an MRI (magnetic resonance imaging) scanner, or another imaging modality. Using an energy source such as x-rays or magnetic fields, for example, the imaging device 120 may capture image data associated with a subject 122 (e.g., a patient).

The imaging device 120 may be controlled by a radiology technician 126 through the use of a workstation terminal or other electronic control 124. Prior to the radiology technician 126 conducting the scan of a patient, information is entered into the terminal 124. In most medical devices, this information must be manually entered via an input device (such as a keyboard) operably coupled to the terminal 124. This information is then placed within the image itself For example, the imaging device 120 may produce radiological images generally consistent with the DICOM format, other industry-accepted standards, or proprietary standards.

Consistent with the appropriate image format, the images produced by the image data source may include metadata. This metadata may be generated by the imaging device 120 and/or by the technician input collected by the terminal 124. Further, the series of images may be obtained directly by the imaging device 120 in the facility shown in FIG. 1A, or may be transferred in whole or in part from another image capturing device connected to the imaging device modality 120 or the facility's local network. The imaging data source may also be transmitted through use of a local facility imaging server (not shown), such as a Digital Imaging and Communications in Medicine (DICOM) server or other PACS.

The metadata within each imaging data file may include identification information such as patient identifier and an identifier of the series of images, in addition to information about the type of modality and the techniques used to obtain the images. Further, for images formatted according to the DICOM standard, data fields such as a unique image identifier, a unique study identifier, the patient's name, and the facility from which the image originates may be included.

The image data generated by the imaging device 120 may include a series of two-dimensional images. In some implementations, the image data may be used to produce a three-dimensional model that can be further manipulated and reformatted for generating two-dimensional (or three-dimensional) images. Image data captured by the imaging device 120 may be stored and processed by the IO management system 102 or another imaging device server (e.g., one or more computers with a processor and a memory), and may be provided to other systems and computers in the system 100 through network 130 (e.g., an intranet or the Internet).

In some implementations, image data provided to the IO management system 102 results in data being stored and processed by one or more computers. For example, the IO management system 102 may determine that the image data is to be forwarded to a system user 142 (e.g., a radiologist) at an image review system 106. As shown, image data may be provided by the IO management system 102 to the image review system 106 through the network 130.

The image review system 106, for example, may include an image display server 144 (e.g., one or more computers with a processor and a memory), a display device 146 (e.g., a monitor), and input devices 148A-B (e.g., keyboards, computer mice, joysticks, touch interfaces, voice recognition interfaces, and the like). In some implementations, image data may be processed by the image display server 144 and visually presented to the user 142 as one or more images at the display device 146. Using the input devices 148A-B, the user 142 may interact with the presented images, for example, by manipulating one or more user controls included in a graphical user interface presented at the display device 146 in association with the images. For example, the user 142 may view an image (or a series of related images), and may specify one or more image adjustments, such as zooming, panning, rotating, changing contrast, changing color, changing view angle, changing view depth, changing rendering or reconstruction technique, and the like. By viewing and interacting with presented image data and with the user interface, for example, the user 142 may produce and indicate a diagnostic finding related to the subject 122.

As further discussed below, when the IO management system 102 receives the image, it may process the image with an image server. This processing may include compressing or converting the image to a different format using a compressor/converter module. This image server may also operate to extract metadata from each image file in a series of radiology scan images. For example, the extracted metadata may include header data for the image providing patient information and hospital information for the hospital that sent the image. The image server may then store all or part of the extracted information in a study record that may be correlated with appropriate orders and studies. The IO management system 102 may operate to pre-populate a radiology order with the extracted metadata, and transmit this radiology order back to the medical facility for verification and submission by a radiology technician or doctor. Such pre-population may reduce the amount of data entry, with the goal of improving the accuracy and speed of the radiology order.

Figure 1B:
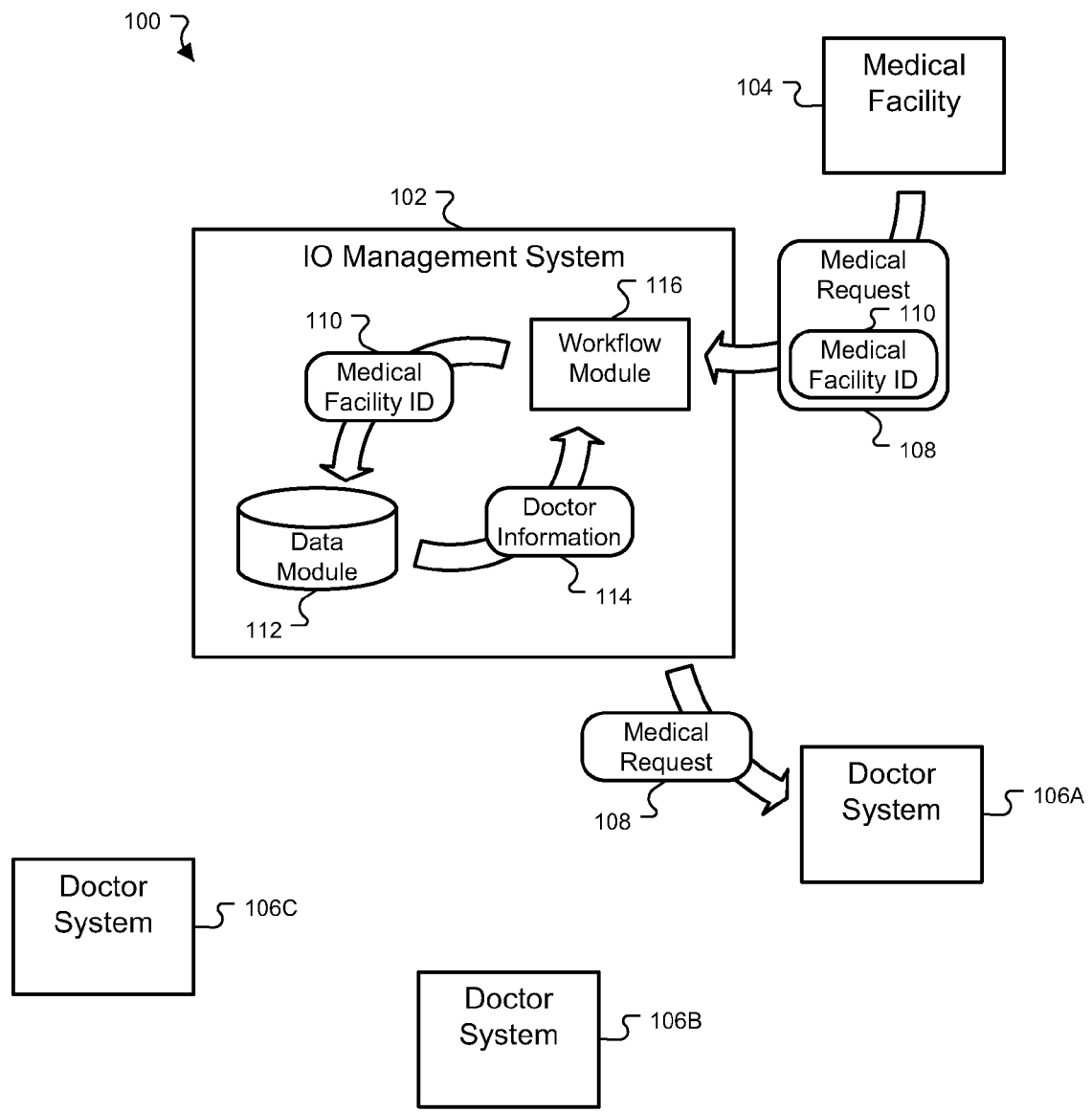
FIG. 1B is a block diagram of a system for assigning medical requests to doctor systems.

As another illustration of operation of the example system 100 for assigning medical requests to doctor systems, FIG. 1B depicts a workflow that may be facilitated by system 100. Medical facilities transmit the medical requests to the IO management system 102, which implements a workflow module that assigns the medical requests to selected doctors. The assignment may be based on several variables, such as whether the doctor is credentialed at the hospital, the doctor's schedule, the preference of the hospital for certain doctors, doctors' licensing status, compensation metrics, online status, geography, performance, and the complexity of previous medical requests that have been assigned to a doctor. After assignment, the IO management system transmits the requests to the assigned doctor.

To implement the medical request assignment, the system 100 includes an IO management system 102, a medical facility 104, and doctor systems 106A-C. The IO management system 102 performs operations to route medical requests from medical facilities, such as the medical facility 104, to one or more of the doctor systems 106A-C. The IO management system 102 receives a medical request 108, which includes a medical facility identifier (ID) 110, from the medical facility 104. The medical facility ID 110 is associated with the medical facility 104 from which the medical request 108 originated.

Figure 3:
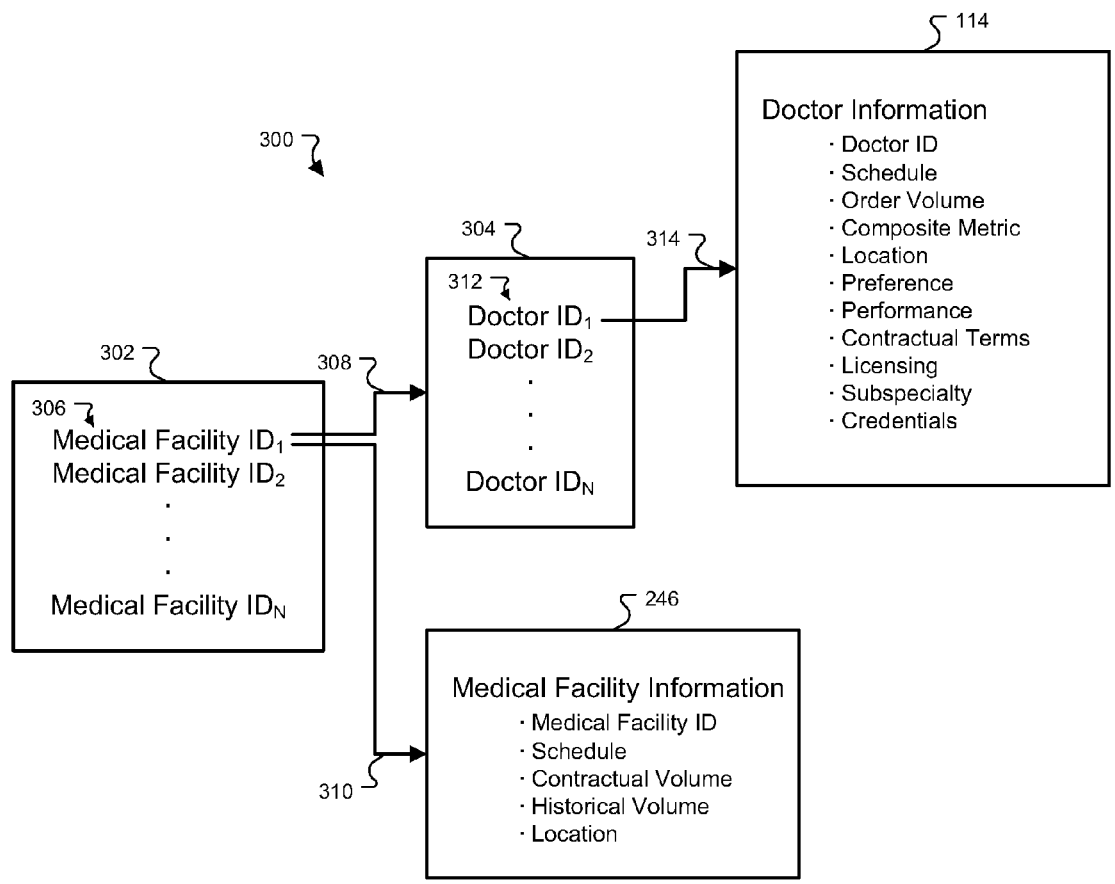
FIG. 3 is a schematic diagram of tables used by a workflow module to assign medical requests.

A data module 112 within the IO management system 102 stores doctor information 114 including a doctor identifier, doctor schedule information, an order volume, a doctor classification composite metric, doctor location information, preference information, performance information, and contract terms (shown in a FIG. 3). For example, a doctor may be identified within the data module 112 by a doctor ID. A doctor's schedule information may include times and dates that a doctor is scheduled to be available for reviewing medical requests. A doctor's order volume may indicate the number of medical requests that a doctor is capable of completing in a given period of time. A doctor's location may determine whether the doctor is allowed to review certain medical requests (e.g. doctors outside the United States may not be allowed to perform a final review of medical images). A medical facility's request for or refusal of a particular doctor may be indicated in the doctor preference information. A doctor's performance may be indicated by the accuracy of the doctor's reports or the satisfaction of medical facilities for which the doctor has reviewed medical requests. The contract terms of a doctor may specify a quota of medical requests the doctor is paid for regardless of the number of medical requests the doctor actually reviews. The contract terms may also specify a bonus rate for medical requests above the quota that are reviewed by the doctor.

A doctor's classification composite metric may be a combination of the doctor's compensation, either per medical request or a salary, and the contract terms of the doctor. In one implementation, a doctor compensated on a per-medical request basis has a lower priority than a doctor that has a quota that has not yet been met. A doctor receiving higher bonus compensation than another doctor would have a lower priority than the other doctor when the two doctors have both reached their quotas. The classification composite metric reduces the overall cost of reviewing a set of medical requests while taking into consideration doctor compensation and doctor contractual terms.

A workflow module 116 receives the doctor information 114 and uses it along with the medical facility ID 110 to filter the medical request 108. In filtering the medical request 108, which is described in greater detail in association with FIGS. 2 and 3, the workflow module 116 identifies a doctor to receive the medical request 108. The IO management system 102 transmits the medical request 108 to the doctor system 106A, which is accessible by the doctor identified during the filtering of the medical request.

To filter the medical request 108, the workflow module 116 transmits the medical facility ID 110 to the data module 112. The data module 112 uses the medical facility ID 110 to access and transmit the doctor information 114 associated with the medical facility ID. For example, the data module 112 may use the medical facility ID 110 as a key in a database table to locate all the doctors credentialed at a hospital specified by the medical facility ID 110. In this implementation, the data module 112 performs a first pass filter by providing to the workflow module 116 the doctor information 114, which contains a list of doctors credentialed at the medical facility 104. In another implementation, the returned list of doctors may be a subset of all the doctors credentialed at the medical facility 104. For example, the data module 112 may only return a list of credentialed doctors that are scheduled to work (as indicated by the doctor scheduling information stored in the data module 112) when the medical facility ID 110 is received by the data module 112.

Figure 2:
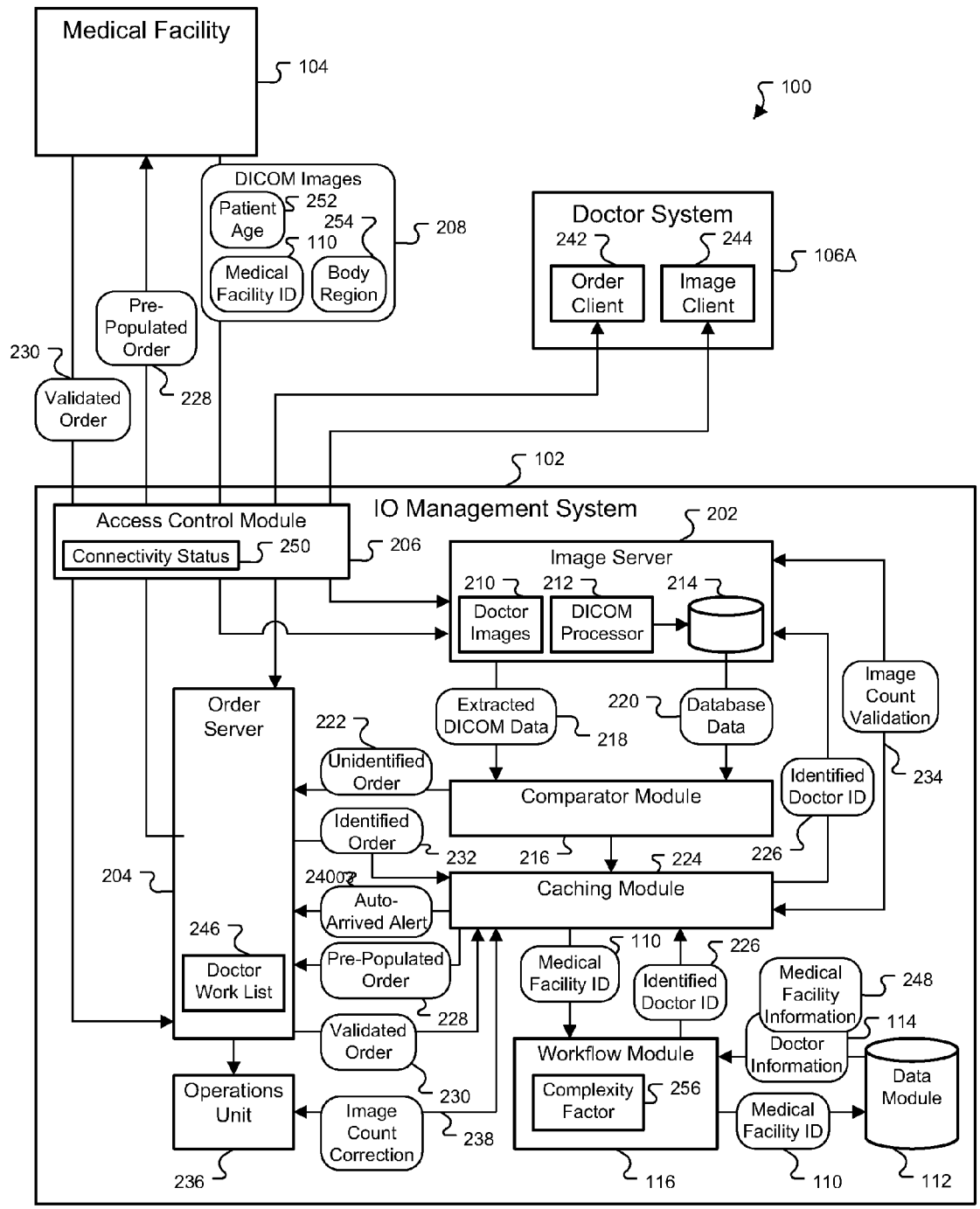
FIG. 2 is a block diagram of the system of FIGS. 1A and 1B in more detail, according to one implementation.

FIG. 2 shows the system 100 of FIGS. 1A and 1B in more detail according to one implementation. Within the IO management system 102, an image server 202 and an order server 204 receive images and orders, respectively, from the medical facility 104. The image server 202 and the order server 204 send the images and the orders to the doctor systems 106A-C for review by the doctors. An access control module 206 provides secure access to the IO management system 102 from the medical facility 104 and the doctor systems 106A-C.

As shown in FIG. 2, the medical facility 104 sends a medical request comprising DICOM images 208 to the IO management system 102. The image server 202 receives the DICOM images 208. The image server 202 may be part of a Picture Archive Communication System (PACS), which digitally stores, transmits, and displays medical images. The image server 202 may store the images as images 210. A DICOM processor 212 extracts DICOM data from the images and stores the DICOM data associated with the images in a database 214. The images are assigned an identifier that is stored in the database 214 and is used to access the images when needed for transmission or other purposes. When received, a compressor (not shown) may compress the images using a variety of compression algorithms to compress the images, such as JPEG, JPEGLS, JPEG2000, PNG, GIF, XBM, BMP, and TIFF.

The compressor may be implemented on the same computing device as the image server 202. In one implementation, the image compressor may be accessible by the software that executes the functions of the image server 202. For example, the image compressor may be a dynamic load library (dll) code segment stored on the same computing device and accessed by the image server 202. Alternatively, the compressor may be implemented on a separate computing device from the image server 202. For example, the compressor may be accessible to software that executes the functionality of an Internet server, which is resident on a separate machine from the image server 202. The Internet server may access the compressor whenever it receives images from the image server 202 for transmission to the network.

Additionally, the database 214 and the images 210 may be stored at the image server 202. For example, the images and database may be stored on same machine that executes the image server software. This may simplify the operation and maintenance of the software. Alternatively, the images and database may be stored on a different machine from the image server. For example, the database may be installed on its own machine that has increased security protections and is isolated from the network in order to protect the medical data stored in the database. Similarly, the images may be installed on a separate machine that provides more storage capacity and specialized hardware that facilitates quick and efficient retrieval and storage of the images. After the workflow module assigns the orders and corresponding images to the selected doctors, the image server 202 may transmit the compressed images over the network to the doctor systems 106A-C.

A comparator module 216 receives extracted DICOM data 218 and database data 220 from the image server 202. The image server extracts the original DICOM data from the images 210 again and transmits it to the comparator module 216 for comparison with the database data 220. The comparison is used to determine if the DICOM processor 212 stored the extracted data correctly and under the correct patient name. For example, if the medical facility ID 110 provided by the medical facility 104 is not unique within the database 214 the workflow module 116 may be unable to provide the correct ID to the data module 112 to filter the medical request. In addition, if a patient name included in the database data 220 and associated with the medical request does not match a patient name specified in the DICOM data 218, then the medical request may be incorrectly associated with the patient. If the medical request is incorrectly associated, then the comparator module 216 sends an unidentified order 222 to the order server 204 for correction. Otherwise, the comparator module 216 provides the medical facility ID 110 derived from the DICOM data included in the medical request to a caching module 224.

The caching module 224 caches information related to the medical request. The caching module 224 transmits the medical facility ID 110 to the workflow module 116. The workflow module transmits the medical facility ID 110 to the data module, which uses the facility ID 110 to access doctor information for doctors credentialed at a medical facility specified by the facility ID. The data module 112 then returns the doctor information to the workflow module 116. Additionally, the data module may return medical facility information 248, such as how many medical requests per day the facility is contracted to request. The workflow module then performs filtering algorithms to determine a doctor to receive the medical requests and returns an associated doctor ID 226 to the caching module. The specific filtering methods used by the workflow module 116 will be described in more detail below. The caching module 224 sends the identified doctor ID 226 to the image server 202. The image server 202 places the images included in the medical request in file folders, or directories, which are associated with the identified doctor ID 226. The caching module 224 generates a pre-populated order 228 using the extracted DICOM data 220 and sends the pre-populated order 228 to the order server 204. The pre-populated order may be an order for a medical service, such as a request to read radiology images that is pre-populated with patient and hospital information, such as the hospital and patient name.

The order server 204 sends the pre-populated order 228 to the medical facility 104. The medical facility 104 validates the information contained in the pre-populated order 228 and sends the validated order 230 to the order server 204. For example, staff at the medical facility 104 may check the pre-populated information for correctness and specify a number of images included in the medical request, a reason for the medical request, and a medical history of the patient. The order server 204 sends the validated order 230 to the caching module 224.

Unidentified orders 222 may also be corrected and then transmitted to the caching module 224. For example, personnel at the medical facility 104 may contact an operator with access to the order server. The medical facility personnel may provide the correct patient identification and other necessary information to correct the unidentified order 222. The operator may then correct the order 222, and the corrected order is transmitted to the caching module 224 as an identified order 232.

In another implementation, the unidentified orders 222 are corrected by transmitting a pre-populated order 228 to a "best guess" medical facility for confirmation. For example, the DICOM information associated with the unidentified order 222 may be used to generate a pre-populated order that includes the patient's name and other extracted information. If the originating facility is uncertain, the order server 204 may use fuzzy logic to determine the medical facility with the highest probability of being the originating facility. The order server may then transmit the pre-populated form with the patient information for confirmation. If the order server determines that more than one medical facility matches information from the DICOM header, the order server may send a pre-populated form to all the matching medical facilities. The confirmed order may then be transmitted to the caching module 224.

As images included in a medical request are received, the caching module 224 queries the image server 202 to determine if the correct number of images have been received, as indicated by arrow 234. If there are either too few or too many images received, then the caching module 224 refers the medical request to an operations unit 236 where the image count is corrected, as indicated by arrow 238. In one implementation, the image count is manually corrected by an operator that may contact personnel at the medical facility to inquire about the image count. When the image count is correct, the caching module 224 sends to the order server 204 an auto-arrived alert 240, and the order associated with the received medical images is placed in the doctor work list 246 associated with the doctor assigned to review the medical request.

The order server 204 sends the validated order 230, which is in the doctor's work list 246, to the order client 242 at the doctor system 106A. The image server 202 transmits the images to an image client 244 at the doctor system 106A. The doctor system 106A is associated with the identified doctor ID 226 and it is accessible by the identified doctor. The doctor may then review the images 208 and the order 230 associated with the medical request. The doctor generates a report based on the review and the report is sent to the medical facility 104, either directly or through the IO management system (not shown).

In filtering the medical requests, the workflow module 116 may use the doctor information 114 and the medical facility information received from the data module 112.

FIG. 3 shows data tables 300 contained in the data module 112. The data tables 300 include a list of medical facility IDs 302, a list of doctor IDs 304, the doctor information 114, and the medical facility information 248. Each medical facility ID is associated with a list of doctor IDs corresponding to doctors credentialed at that medical facility. Here, a first medical facility ID 306 is associated with the list of doctor IDs 304, as indicated by arrow 308. Each medical facility ID is associated with medical facility information. Here, the first medical facility ID 306 is associated with the medical facility information 248, as indicated by arrow 310. Each doctor ID is associated with doctor information. Here, the first doctor ID 312 is associated with the doctor information 114, as indicated by arrow 314.

The doctor information 114 may include data as described in association with FIGS. 1A and 1B. The doctor information 114 may also include credentialing and subspecialty information. In one implementation, the workflow module 116 may use the credentialing, the subspecialty information, or both to filter the medical requests. For example, a doctor that is not credentialed at the medical facility 104 will not be allowed to review medical requests from the medical facility 104. A doctor having a subspecialty in a particular type of medical request, such as a review of a magnetic resonance imaging (MRI), will be selected over another doctor having similar information, but no subspecialty in MRI reviews. In another implementation, the data module returns the entire doctor list 304. The entire list of doctors may be eligible to review the images because all doctors in the list 304 are credentialed at the medical facility associated with the facility ID 306.

The medical facility information 248 includes schedule information, location information, or both. The workflow module 116 may use the medical facility schedule information, the medical facility location information, or both to filter the medical requests. For example, a medical request received from the medical facility 104 outside of its scheduled service time may be categorized as an unidentified order 222, which prompts staff at the IO management system 102 to investigate the medical request. In another example, if the medical facility 104 is located within the United States and the medical request is a final reading of medical images, then a doctor located within the United States must be assigned to the medical request.

Referring again to FIG. 2, the access control module may monitor a connectivity status 250 of the medical facility 104 or the doctor systems 106A-C. The connectivity status 250 may indicate whether an encrypted network connection used by the medical facility 104 or the doctor systems 106A-C is operational. The workflow module 116 may use the connectivity status 250 of the medical facility 104 or the doctor systems 106A-C when filtering the medical requests. For example, the workflow module 116 may determine from the connectivity status 250 that the network connection to the doctor system 106A is not operational. The workflow module 116 may prevent medical requests from being assigned to the doctor associated with the doctor system 106A and assign the medical requests to the next doctor available based on the filtering rules.

The workflow module 116 may monitor the doctor work list 246 to determine the number of medical requests assigned to and not yet completed by the doctor. The workflow module 116 may use the number of incomplete medical requests to filter the next medical request. For example, a doctor with a high number of incomplete medical requests may have a lower chance of being assigned another medical request than a doctor with a low number of incomplete medical requests.

The DICOM images 208 may include information in DICOM headers, such as a patient age 252 and a body region 254. The workflow module 116 may determine a complexity factor 256 of the medical request based on the patient age 252, the body region 254, and the medical facility ID 110. For example, an image depicting a head or a chest may be more difficult for a doctor to review than an image depicting a forearm or leg. In addition, a medical request for a patient less than two years of age or over 75 years of age may be more difficult to review than a medical request for a patient that is 25 years old. Also, some medical facilities associated with a medical facility ID 110 may consistently transmit complex or difficult medical requests. Some or all of these factors may be combined to generate the complexity factor 256.

In one implementation, the workflow module 116 assigns weights to each of the components used to calculate the complexity factor 256. The weights may range from −1 to 1, with −1 being associated with less complexity and 1 with more complexity. For example, a patient that is 72 years old may have a weighting of 0.9, which indicates the case is more complex. In contrast, a 30 year old patient may have a weighting of −0.9, which indicates the case is less complex. The complexity factor may be the sum of the weightings for each component.

The workflow module 116 may use the complexity factor 256 to prevent a doctor from accepting only those medical requests that are easy. If the average complexity of the medical requests in the doctor work list 246 is low, then the workflow module 116 may assign only complex medical requests to the doctor until the average complexity of the doctor work list 246 meets a threshold. Similarly, if a doctor has accepted several complex medical requests, the workflow module may assign requests with a lower complexity factor to that doctor.

In one implementation, the threshold may be a single number that is compared with the sum of all the complexity factors. For example, a doctor may accept three difficult cases, each with a complexity factor of 2.9, and five simple cases, each with a complexity factor of −0.7. This means that the doctor has a complexity total of 5.2. If the threshold is 10, the workflow module may assign the doctor difficult cases until the threshold is met. If the threshold is exceeded, the workflow module may assign the doctor simple cases until the complexity total reaches or comes within a predefined range of the threshold. In another implementation, the threshold may be a number of studies that exceed a defined complexity factor. For example, if the doctor accepts four cases per hour with complexity factors over 2.5, the workflow module will assign simpler cases with complexity factors under −1.2 to the doctor until the hour is over.

In one implementation illustrating how the workflow module 116 obtains and uses the doctor information and the medical facility information to filter requests, the medical facility 104 sends images to the image server 202. The images include DICOM header information recording the patient's age, the body region with which the images are associated, and the medical facility ID.

The image server 202 extracts the DICOM information listed above and transmits it to the workflow module 116. The workflow module transmits the medical facility ID to the data module 112, where it is used to locate an entry that matches the facility ID. The matching entry may have a list of doctor identifiers that are credentialed at the medical facility specified by the medical facility ID. The doctor identifiers, in turn, may have doctor information, such as schedule information, volume information, performance information, and a complexity total, associated with each doctor identifier's entry. The data module 112 may then return to the workflow module the doctor identifiers of the doctors credentialed at the identified hospital and the associated doctor information.

The workflow module may then begin the filtering process with a first of several rules that are applied to determine which doctor to assign the medical requests to for review. For example, the first filter rule may determine which of the credentialed doctors is available to accept medical requests using the doctors' schedule information, which indicates the doctors that are currently on-call to accept requests.

Then the workflow module may apply a second rule that determines which of the on-call doctors have a functioning network connection to the IO management system 102. The on-call doctors that are currently connected (as monitored by the workflow module) will remain in a pool of doctors eligible to receive the medical request, while the doctors that are not actively connected are eliminated from the pool.

The next rule may consider the volume of medical request the doctors have currently accepted, but not completed (as indicated by the volume information received from the data module). In one implementation, the doctors with the least volume will be favored with a weighting factor over doctors with higher volume. For example, the workflow module may assign a weighting factor that favors doctor A over doctor B if doctor A has four accepted but incomplete medical requests, and doctor B has five accepted but incomplete medical requests.

The next filter rule may consider performance of the doctors, such as the average time it takes from acceptance to completion of a request (as indicated by the performance information received from the data module). In one implementation, the doctors with the shortest performance times are favored over doctors with longer performance times. In another implementation, the filter rule may be used in cooperation with the volume filter rule to determine a weighting for each doctor. If doctor A has a volume of four, and doctor B has a volume of five, the workflow module may still assign a weighting that favors doctor B over doctor A because doctor B has performance information that indicates doctor B will complete the medical requests in less time than doctor A. For example, if doctor A can complete four medical requests in an hour, but doctor B completes five medical requests in 50 minutes, doctor B is assigned a favored weighting because doctor B will be ready to review another medical request before doctor A, despite the fact that doctor B as more medical requests.

Additionally, the workflow module may implement a complexity filter that calculates a complexity factor for the medical request and assigns a weighting that favors or disfavors a doctor depending on the doctor's complexity total, which reflects the complexity of the cases that the doctor has accepted in the past. The workflow module may calculate the complexity factor for the medical request in a manner similar to the manner described above. The workflow module compares the doctor's complexity total to a threshold value, which is also described above. The workflow module then assigns a weight favoring or disfavoring each doctor depending on whether the doctor's complexity total reaches a threshold value and whether the medical request to be assigned is complex or simple as determined by the workflow module.

For example, the workflow module determines that the medical request is complex based on the age of the patient, the body region scanned, and the originating medical facility. The workflow module then determines that doctor A has not met the threshold, which indicates the doctor has not accepted enough difficult cases. The workflow module will then assign a weight favoring the assignment of the medical requests to doctor A over other doctors that have exceeded the threshold, which indicates these doctors have accepted more difficult cases than doctor A.

After the workflow module applies the filter rules, the module sums the weighting factors for each of the doctors remaining in the assignment pool. The workflow module then selects the doctor with the highest weighting to receive the medical request.

Figure 4:
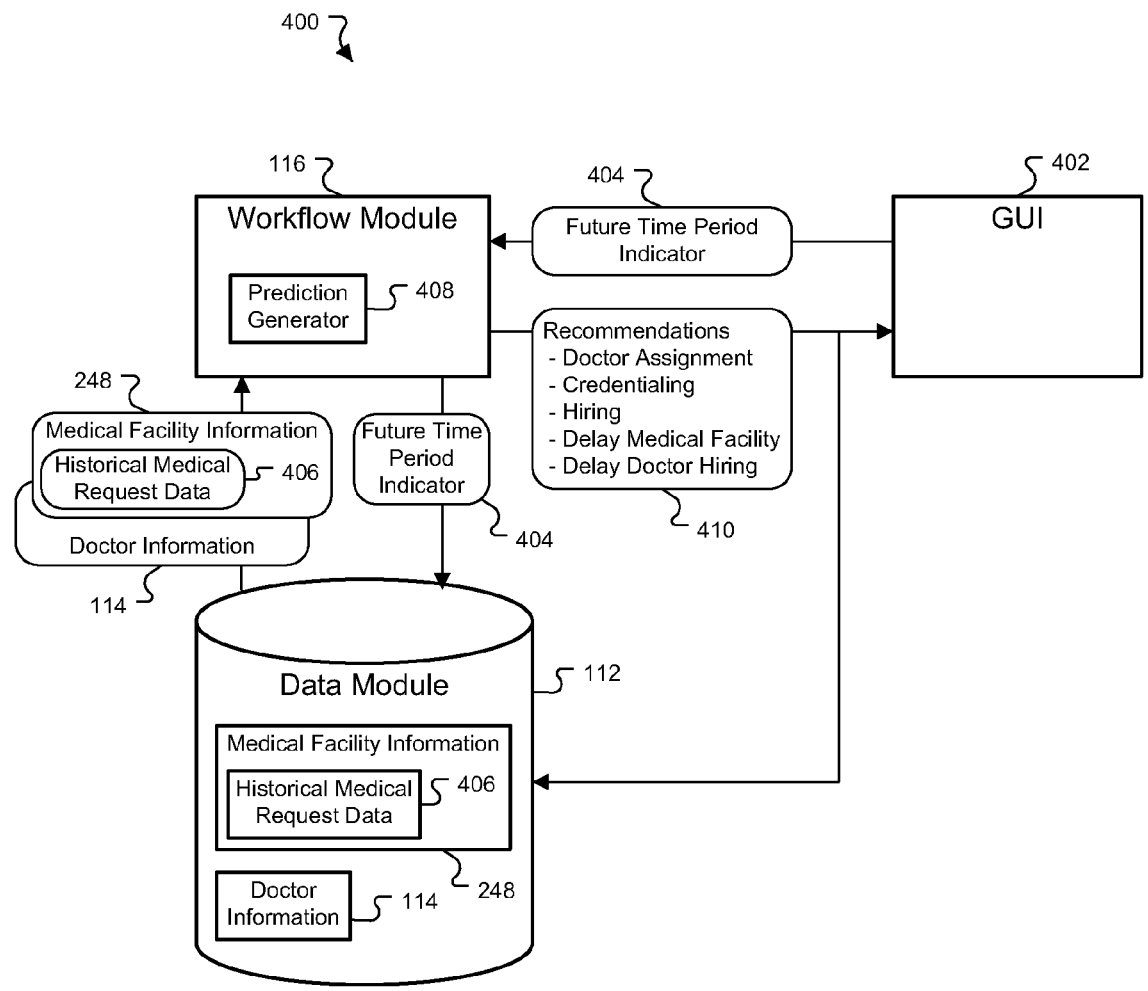
FIG. 4 is a block diagram of a portion of an image order management system that predicts an amount and origin of future medical requests.

FIG. 4 shows a system 400 that may be included in the IO management system 100. The system 400 is capable of predicting an amount and origin of future medical requests. This information, in turn, may be used to ensure enough doctors are available to handle the predicted number and type of medical requests. Additionally, the information may be used to identify if more medical requests are needed to fully utilize the predicted amount of doctors available to review the requests. The system 400 includes a graphical user interface (GUI) 402, the workflow module 116, and the data module 112.

More specifically, a user uses the GUI 402 to enter an input that indicates a future time period 404 for the prediction. The indicator 404 may describe a particular date in the future. The workflow module 116 receives the future time period indicator 404. The workflow module 116 queries the data module 112 using the indicator 404. The data module returns medical facility information 248 and doctor information 114 associated with the future time period indicator 404. The medical facility information 248 may include data describing all of the medical facilities that are scheduled to submit medical requests on the date and time in the future. The doctor information 114 may include data describing all of the doctors that will be online and scheduled to work on the date in the future. Here, the medical facility information 248 also includes historical medical request data 406.

For example, the future time period indicator 404 may indicate a particular day of the week within the following week, such as next Wednesday. The data module 112 may return historical medical request data 406 information regarding medical requests received from each medical facility for the two previous Wednesdays. The data module 112 also returns the doctor information 114 and the other medical facility information 248 previously described for filtering medical requests.

A prediction generator 408 in the workflow module 116 may use the historical medical request data 406 to generate a prediction for the amount and origin of medical requests occurring during the future time period. The prediction may indicate the average number of medical requests received per hour from a particular medical facility on a particular day of the week.

In another implementation, the prediction generator 408 uses contractual information associated with each of the medical facilities to generate the prediction. For example, the prediction generator may use an indicator specifying a future time period to determine what facilities are contractually obligated to submit requests during the period. The generator may transmit the indicator to the data module 112, which returns the medical facility IDs of facilities scheduled to submit request and the information associated with the medical facilities including contract terms. The generator may create a prediction based on how many requests each medical facility has contracted to submit.

The allocation may be an approximately equal division of requests per hour. For example, if a medical facility is contracted to submit 40 medical requests on a day specified by the indicator, the generator may allot a portion of the requests to each hour that the medical facility is contracted to submit requests (e.g., 5 requests allocated to 7 PM, 5 requests to 8 PM, etc.). Alternatively, the generator may allocate the requests on a bell curve model so that fewer of the requests are allocated near the beginning and the end of the scheduled submission hours, and more requests are allocated during the intermediate hours.

In another embodiment, the prediction generated by the prediction generator 408 is based on long-term patterns, such as seasonality. The prediction may incorporate the average number of medical requests submitted by medical facilities during the month or week of the preceding years relative to the time period indicator. For example, if the indicator is for a day in December 2005, the generator may generate a prediction for this day using the average number of requests submitted daily by medical facilities in December 2004. Additionally, the generator 408 may weight this prediction using a growth factor, which accounts for growth in submitted medical requests. For example, the generator may determine based on historical data associated with medical requests that the average number of submitted requests has grown on average 27 percent a year for the past year. Applied to the previous example, this growth factor may be used to increase the seasonal prediction for December 2005 so that it is 27 percent higher than it was in December 2004.

In yet another embodiment, the prediction generator 408 may be used for scheduling. The generator may use the predicted medical requests to determine which doctors have the appropriate credentials to fulfill the predicted medical requests, and it may transmit a recommendation to a user that describes which doctors should be scheduled for which times. For example, if the prediction indicates that St. Mercy Hospital will submit 10 medical requests at 10 PM on Apr. 1, 2006, then the generator may recommend (or automatically schedule) that Doctor A, who is credentialed at St. Mercy, be scheduled to work at 10 PM on that day.

Figure 5:
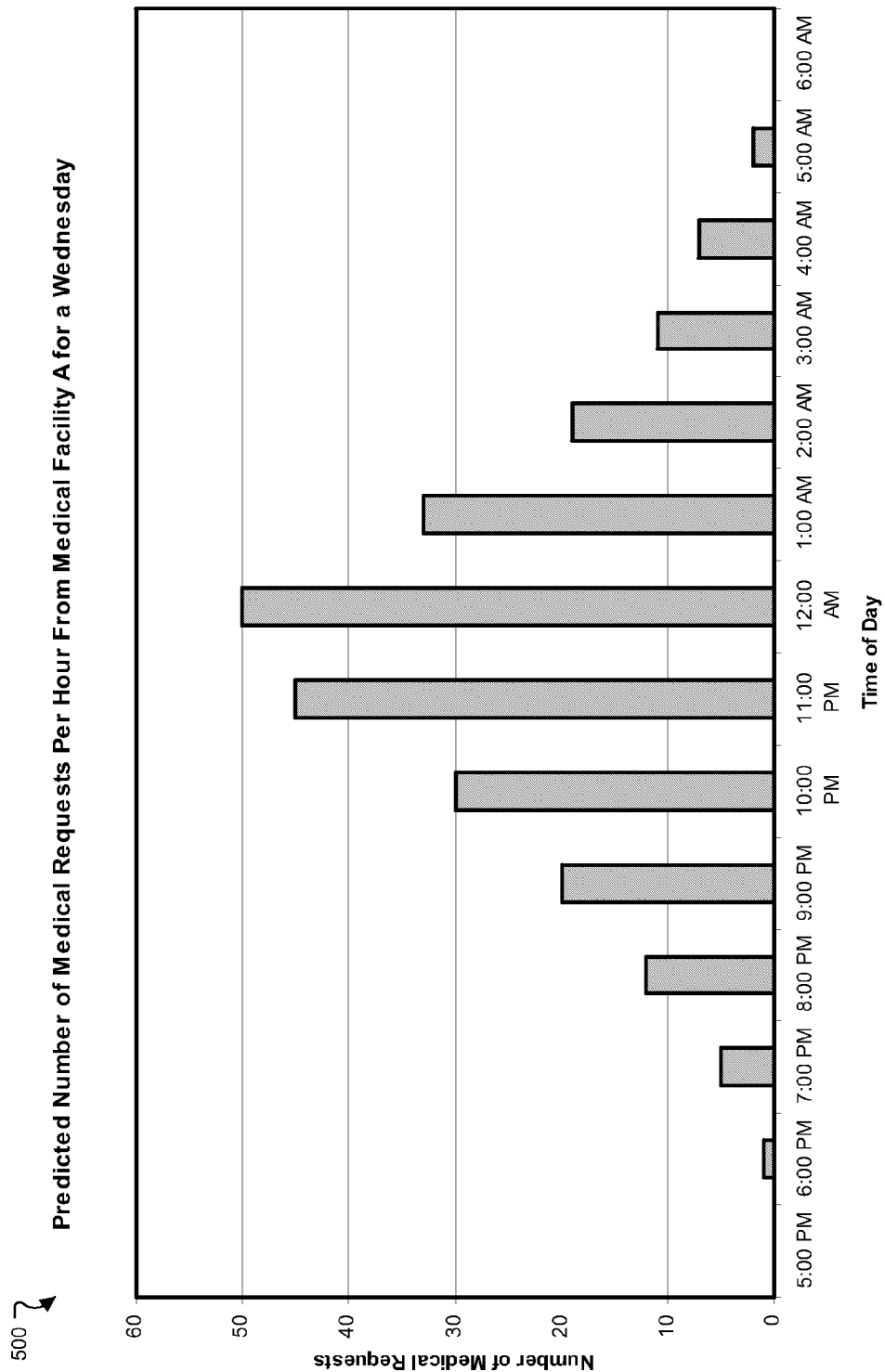
FIG. 5 is a graph showing an example prediction from a prediction generator implemented at the image order management system.

As shown in FIG. 5, the prediction generated by the prediction generator 408 may be illustrated using a graph 500 including the number of medical requests per hour from a particular medical facility for a particular day of the week. Here, the graph 500 shows the number of medical requests per hour from Medical Facility A for the two previous Wednesdays. Based on the historical medical request data 406 for Medical Facility A, one can see that on average Medical Facility A begins to send medical requests at 6:00 PM. The number of medical requests from Medical Facility A peaks at 12:00 AM and Medical Facility A no longer sends medical requests after 5:00 AM on the morning after a Wednesday.

Referring again to FIG. 4, the workflow module 116 assigns the future medical requests to doctors in a similar manner as described in FIGS. 1B and 2. Each predicted medical request is processed as if it had been received by the IO management system 102. The workflow module 116 may use the doctor information 114, including doctor performance information, such as turnaround time for reviewing medical requests, to determine how long a medical request should remain in a doctor's work list. New medical requests may be added to the doctor's work list based on the doctor's historical rate of the fulfilling medical requests.

In some implementations, the medical facility information 248 is associated with medical facilities that are not yet active within the system 100. The prediction generator 408 may use information within the medical facility information 248, such as the date that a medical facility will become operational within the system 100, to make its prediction. If the future time period occurs after a new medical facility will become active, then the prediction generator 408 may use an average of the other medical facilities to determine the number of medical requests the medical facility is likely to transmit. The prediction may indicate an average number of requests generated in the past by a typical medical facility during the indicated time period. For example, a medical facility may be scheduled to send medical requests for the first time during the indicated time period. In this situation, the medical facility will not have a set of past medical requests which the prediction generator 408 may use to generate a prediction. To mitigate this problem, the prediction may be based on an average of the number of combined medical requests submitted by other medical facilities during the indicated time period. For instance, if 5 hospitals send 40 requests at 7 PM last Wednesday, then the average for last Wednesday would be 8 requests at 7 PM. The prediction based on the average requests submitted by the other facilities serves as a substitute when historical information for requests is not available for a particular medical facility.

In some implementations, the workflow module 116 recursively reassigns the future medical requests to the doctors until the assignments produce an optimal assignment. The workflow module 116 may determine the optimal assignment based on whether a value associated with assignment is below a threshold or within a defined tolerance range. A particular set of choices for doctor assignments may result in one or more medical requests that cannot be assigned to a doctor. For example, a medical request from Medical Facility A may remain unassigned if the only doctor scheduled to work during that time who is credentialed at Medical Facility A already has a full work list. The workflow module 116 may go back and reassign the medical requests. During the reassignment, the workflow module 116 may make a different choice regarding medical requests assigned to the doctor credentialed at Medical Facility A.

A reiterative assignment process may continue until a threshold is met. For example, the threshold may be that zero medical requests are left unassigned. The assignment process will go through multiple iterations until a state is reached where all the medical requests are assigned. Alternatively, the reiterative assignment process may continue until a certain number of iterations have been performed. After this number is reached, the state with the lowest number of unassigned medical requests may be selected, and a recommendation (discussed in greater detail below) may be generated that informs a user what actions the user needs to take to avoid unassigned medical requests, such as hire a doctor credentialed at the hospital or hospitals with the unassigned request or requests.

In some implementations, the workflow module 116 generates recommendations 410 that may be based on the predictions. For example, if attempts at reassignment identify predicted medical requests that can not be assigned because doctors are not available to review the requests from a particular medical facility, then the workflow module 116 may recommend that more doctors be credentialed at the medical facility. If there are not enough doctors to review all of the medical requests even if the active doctors are credentialed at facilities with unassigned medical requests, then the workflow module 116 may recommend that more doctors be hired. If the work lists of doctors are consistently low, then the workflow module 116 may recommend that more medical facilities be recruited for the system 100.

In addition, the workflow module 116 may recommend that the integration of new doctors be delayed if the workflow module makes predictive assignments that indicate active doctors do not have enough medical requests to review. For example, if the predicted assignments indicate that each of the existing doctors is only assigned 45 medical requests in a shift, the workflow module may recommend that new doctors should not be allowed to enter the system until the existing doctors are each assigned 55 medical requests in a shift. Similarly, the workflow module 116 may recommend that new medical facilities be delayed if the workflow module generates predictive assignments that indicate active doctors have too many medical requests to review. For example, if the predicted assignments indicated that each of the doctors is assigned 100 medical requests in a shift, the workflow module may recommend that new medical facilities should not be allowed to enter the system until more doctors are hired.

In some implementations, the workflow module 116 stores and uses the previously predicted assignments when the future time period occurs. The workflow module 116 may use the predicted sequence of medical request assignments as a starting point when assigning medical requests in real-time. If the predicted assignment does not apply or is invalid based on the current state of the system 100, the workflow module 116 may revert to the filtering rules as described in FIGS. 1B and 2. For example, when a medical request is received by the IO management system, the workflow module may make an assignment based on the stored predicted assignment without reapplying any of the filtering rules. If the current state of the system 100 is different from the predicted state of the system (e.g., one of the on-call doctors is not currently connected, an additional hospital is submitting medical requests, etc.), then the workflow module 116 uses the filter rules to make new assignments instead of using the predicted assignments.

Figure 6:
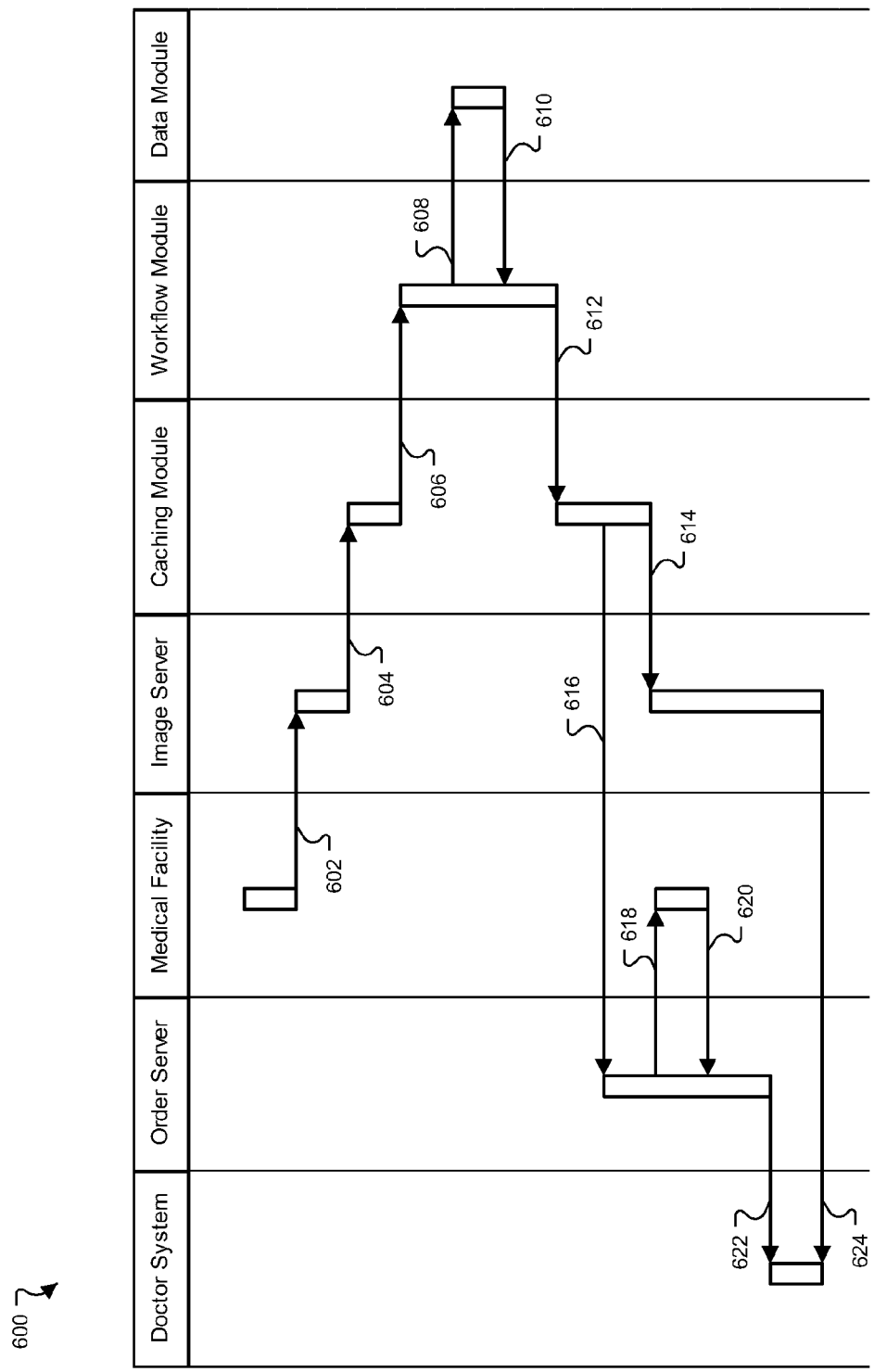
FIG. 6 is a sequence diagram of example operations that can be performed to assign medical requests to doctor systems.
Figure 7:
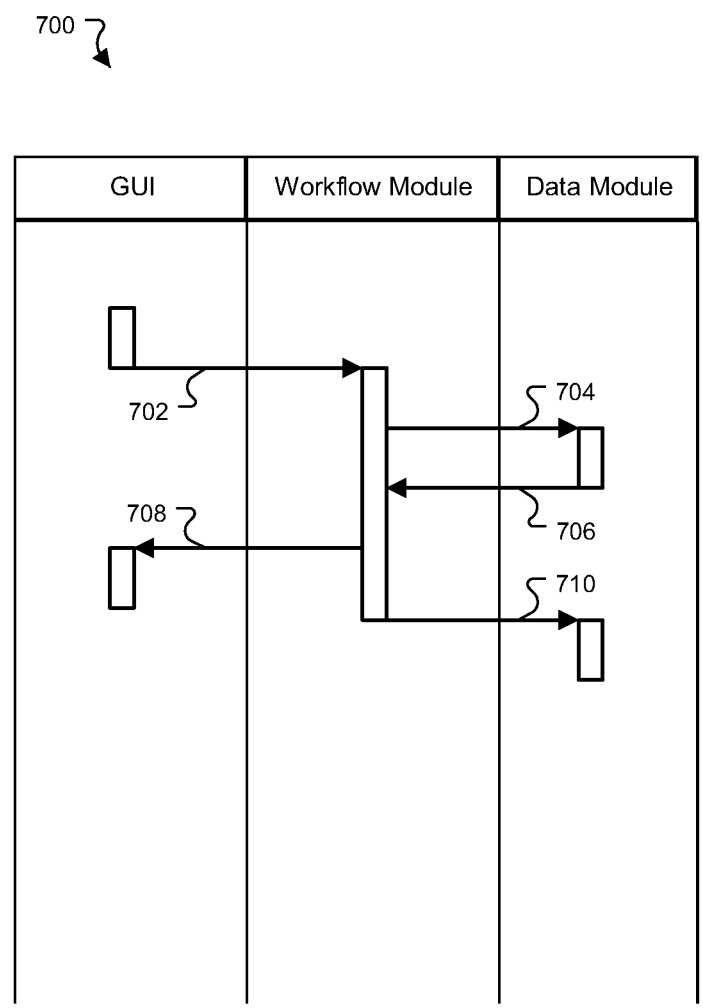
FIG. 7 is a sequence diagram of example operations that can be performed to predict an amount and origin of future medical requests.

FIGS. 6 and 7 are sequence diagrams illustrating example methods 600 and 700, respectively, for assigning medical requests to doctor systems and predicting future medical requests, respectively. Generally, the following description focuses on the operation of the IO management system 102 within the system 100. However, the operations contemplate using any appropriate combination and arrangement of logical elements implementing some or all of the described functionality.

FIG. 6 shows an example sequence of operations 600 that the system 100 can perform to assign medical requests to doctor systems. The operations 600 begin with the medical facility 104 sending a medical request, such as the DICOM images 208, as indicated by arrow 602. The image server 202 within the IO management system 102 receives the DICOM images 208.

The image server 202 stores the DICOM images 208 and extracts DICOM data 218 from the DICOM images 208. The extracted DICOM data 218 is stored in a database 214. As more images in the medical request are received, the database data 220 is compared to the raw (not yet stored in database 220) extracted DICOM data 218. If they do not match, then the medical request is invalid and the image server 202 sends the unidentified order 222 to the order server 204. Otherwise, the DICOM images 208 are sent to the caching module 224, as indicated by arrow 604.

The caching module 224 sends the medical facility ID 110 contained in the DICOM images 208 to the workflow module 116, as indicated by arrow 606. The workflow module 116 uses the medical facility ID 110 to query the data module 112, as indicated by arrow 608.

The data module 112 returns the doctor information 114 to the workflow module 116, as indicated by arrow 610. The doctor information 114 may include a list of doctors and information associated with the doctors, such as the doctor's schedule, order volume, and contractual terms. The data module 112 may also return medical facility information 248, such as a medical facility location and a medical facility schedule.

The workflow module 116 filters the medical request to assign a doctor to the medical request. The filtering may be based on doctor information 114 and medical facility information 248 as described in association with FIGS. 1B and 2. In some implementations, the workflow module 116 may assign more than one doctor to a medical request or the workflow module 116 may later reassign the medical request. This double assignment and reassignment of medical requests decreases the probability that a request will remain incomplete for an unacceptable period of time.

For example, a backup doctor may always be assigned in addition to the normally assigned doctor or if a medical request is not completed in a certain amount of time, the workflow module 116 may reassign the medical request to another doctor or an additional doctor. For example, the workflow module may assign the medical request to doctor #1 and not to doctor #2. However, reassignment may include revoking the assignment of the medical request to doctor #1 and assigning the medical request to doctor #2. Alternatively, the reassignment may include assigning the medical request to doctor #2 as well as to doctor #1. The workflow module 116 sends the identified doctor ID 226 to the caching module 224, as indicated by arrow 612.

The caching module 224 creates a pre-populated order 228 using the extracted DICOM data 218. The caching module 224 sends the identified doctor ID 226 to the image server 202 and the caching module 224 sends the pre-populated order 228 to the order server 204, as indicated by arrows 614 and 616, respectively.

The order server 204 sends the pre-populated order 228 to the medical facility 104, as indicated by arrow 618. The medical facility 104 validates the pre-populated order 228 and sends the validated order 230 to the order server 204, as indicated by arrow 620. The validation may include specifying a total number of images in the medical request, the reason for the medical request, and a medical history of the patient.

The order server 204 sends the validated order 230 to the caching module 224 where the expected number of images in the medical request is compared to the number of images received. If all of the images are received, the order server 204 places the validated order 230 in the work list 246 of the identified doctor and transmits the validated order 230 to the doctor system 106A, as indicated by arrow 622. The image server 202 places the DICOM images 208 in the doctor's directory associated with the identified doctor ID 226. The image server 202 sends the DICOM images 208 to the doctor system 106A, as indicated by arrow 624.

Again, FIG. 7 is a sequence diagram that illustrates an example method 700 for predicting future medical requests. The operations 700 begin with the user input of a future time period indicator, such as a day or week in the future. A user may make the input through the GUI 402. The workflow module 116 receives the future time period indicator 404, as shown by arrow 702.

The workflow module 116 queries the data module 112 using the future time period indicator 404, as indicated by arrow 704. For example, the workflow module 116 may request, using the future time period indicator 404, all of the historical medical request data 406 for a particular day. The historical medical request data 406 may include an indicator of all the medical requests sent by the selected medical facilities on the particular day in prior weeks, months, or years. The medical facilities are selected based on their schedules and their online status. A medical facility is selected if it is scheduled to submit medical requests and it is online during the future time period.

The data module 112 returns the historical medical request data 406 associated with the future time period indicator 404, as indicated by arrow 706. The data module 112 also returns the doctor information 114 and the medical facility information 248, which is used by the workflow module 116 to assign the medical requests to a selected doctor.

The workflow module 116 uses the historical medical request data 406 to generate a prediction of an amount and origin of medical requests that will occur during the future time period. The workflow module 116 uses the assignment rules described in FIGS. 1B and 2 to assign all of the predicted medical requests for the future time period. The workflow module 116 may output recommendations 410 based on the assignments to a user of the GUI 402, as indicated by arrow 708.

The workflow module 116 may store the assignment information or the recommendations 410 in the data module 112. The workflow module 116 may use the assignments, the recommendations 410, or both when the future time period occurs.

In a further embodiment, predictions of future medical requests and service recommendations to meet future medical requests may be generated from a set of customized models and scenarios. In particular, the data produced by a constraint-based system such as the multiple resource planning system described herein may be queried by a user (such as an administrator or planning staff) to produce more accurate recommendations and forecasts applicable to future usage of the resources.

As further described herein, the multiple resource planning system may include a modeling engine. The modeling engine may receive a plurality of inputs from a user to test out the response of the workflow module and generate recommendations for future activities based on hypothetical or real scenarios. For example, the modeling engine may be used to generate a forecast to determine what happens to the availability of medical resources if a 10 percent increase in the radiology reads would occur during a holiday period. This 10 percent increase might be calculated from historical demand for services over this particular holiday, or provided as a hypothetical scenario to test the flexibility of available resources.

Additionally, the modeling engine may be used to factor one or more real world scenarios and expected future events and generate a resulting schedule. For example, in connection with a teleradiology workflow, the modeling engine may generate a resource forecast from the addition of one or more radiologists at a future point in time. The radiologist might be available only during certain days or time periods, or may become available only after some future time (such as when the radiologist becomes an available resource after an expected date of licensing or credentialing approval). Alternatively, the modeling engine might be used to estimate and factor the demand from a new medical facility which is scheduled to consume medical services at a future point in time.

Based on the forecasting results of the modeling engine, a radiology services provider may respond accordingly. For example, the radiology services provider may recognize a need to call in additional radiologists or staff based on the updated forecasts. These forecasts may be designed to factor in excess staffing levels throughout a wider period of time, and also filling in any resource needs based on the preferences and restrictions of the medical facility. Likewise, the radiology services provider may recognize that certain specialties are understaffed and need to be filled, or that additional licensing and credentialing must occur by certain radiologists to meet estimated demand.

Figure 8:
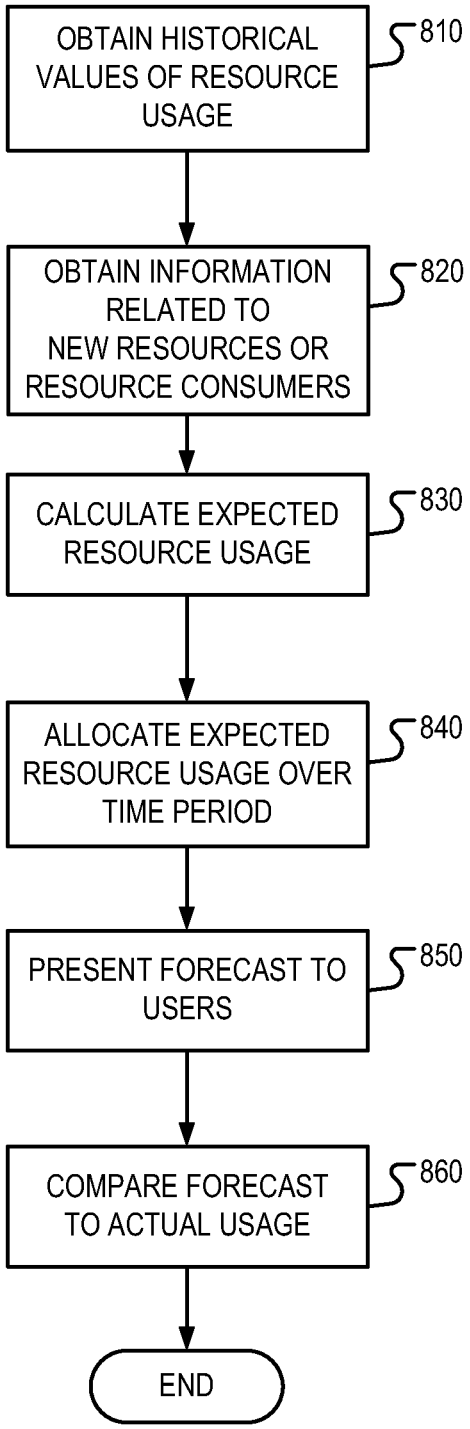
FIG. 8 is a flowchart of example operations that can be performed for medical request and doctor resource planning and forecasting techniques with use of a modeling engine.

As a more specific example, with use of the modeling engine, a forecasting process may be initiated to create a proposed schedule and predict a shortfall or excess in the number of hospital credentials, state licenses, or radiologists needed to fulfill a projected volume of future radiology read requests during a future date or dates. FIG. 8 illustrates a flowchart for enhanced multiple resource planning and forecasting 800 with use of a modeling engine according to one embodiment of the present invention. The illustrated flowchart demonstrates how a forecast may be created and customized based on a series of data inputs and resource usage computations.

Two sets of data may be factored within the enhanced forecasting data model. First, historical values of the resource usage 810 are provided as the primary input to the data model. As previously discussed, in a teleradiology setting this may be an average of the historical number of medical requests (such as teleradiology reads) performed for a medical facility or a set of medical facilities during a defined time period, along with the efficiency and capacity of existing radiologist resources.

The historical values of the resource usage may be further characterized based on the facility attributes of a medical facility that correlate to its resource usage. For example, the number of specific requests may directly or indirectly correlate to the medical facility size, number of medical imaging devices, geographic region of the medical facility, regional demographics, regional population, requested subspecialties, and like factors. Therefore, when attempting to obtain historical data, the modeling engine will cluster data input and resource usage from similar facilities and resource usage scenarios.

Second, future information related to resources or resource consumers 820 (i.e., expected changes) is obtained and provided as input. For example, this may be information related to the capabilities of a new resource such as the addition of a new radiologist capable of reading a defined volume of radiology images, or information related to the expected amount of new medical requests from new medical facilities or sites coming online. This future information, especially for new medical facilities, may be estimated by data modeling. A comparison of the common characteristics of similar medical requests or medical facilities (such as same hospital size and served population) may provide a reliable estimation of demand for an incoming medical facility.

In a teleradiology setting, algorithm inputs extracted from historical and future information may produce data associated with one or more of the following data model constraints. A non-limiting list of constraints and the historical or predicted data values that may be factored in the forecasting data model includes: facility order volumes (historical rates at an hourly level), order types, radiology modality and procedure types (which may correspond with radiology subspecialties), uplifts (percentage adjustments for particular days, such as holidays), medical facility preferences, radiologist preferences, medical facility or radiologist restrictions, specialty constraints and preferences, radiologist efficiencies and reading capacities (which may be derived from historical data, in the form of how many reads per hour or per time period were completed, or a comparison of productivity during nighttime versus daytime shifts), radiologist schedules and schedule customizations (such as scheduled time off, extra shifts, shift extensions, and tolerance of schedule changes), coverage hours for medical facilities (which may be based on a schedule or contractual obligations), contracted and scheduled hours for radiologists, radiologist licensing qualifications and restrictions in particular jurisdictions (e.g., state by state licenses), radiologist credentialing and restrictions in each medical facility, radiologist costs (such as radiologist compensation determined from a combination of compensation algorithms and metrics that provide for radiology read quotas and bonuses), radiologist location (whether the radiologist is working directly at the medical facility or in a particular jurisdiction), insurance provider rules (which may include radiologist location for billing purposes, and whether a radiologist is qualified to perform the radiology read in the provider network or according to provider rules), expected licensing of radiologists occurring at a future time, and expected credentialing of radiologists occurring at a future time.

Even if the number of data attributes selected for use in the forecasting model is fairly small, the volume of historical data entries to parse and evaluate may be extremely large. The analysis of a large set of data is useful to overcome variations in data that are intrinsically tied to the fluid nature of demand for medical procedures. A medical facility may produce more or less demand than a medical facility of the identical size for a variety of reasons. Therefore, filtering the data inputs by a plurality of constraints and selecting more data entries with common attributes may obtain a more accurate picture of relevant historical data.

A large volume of data inputs may be evaluated within the data model to produce an averaged or estimated data set that excludes or diminishes the impact of outlier and exceptional data events. As explained below, data input filtering by constraints may be used to not only predict resource usage and demand related events but also to create a robust schedule of radiologists to address the forecasted demand. The filtering techniques are particularly useful when applied to data inputs such as scheduling data narrowed to a specific date or date range. The main factors that are balanced from historical and future information are demand from medical facilities and radiologist reading capacity; however any of a number of the previously described constraints may be employed to generate an accurate data model representation.

Based on the historical and future information factored within the data model, the expected resource usage is calculated as in step 830. In one embodiment, calculating the expected resource usage is performed by running a regression on the data inputs and modeling orders for a set number of hours. For example, demand may be modeled in 4 hour chunks. This data may then be provided to a forecast data mining model for further comparison and refining. In another embodiment, the expected resource usage may be calculated hour-by-hour for one or more days.

As in step 840, the expected resource usage forecast for a time period is shaped and further refined with use of a data mining model. For example, a 4-hour interval volume for a set of medical facilities may be computed and segmented by facility, procedure, or the day of week. The total volume for all of the medical facilities is shaped with the forecast data mining model derived from the historical and forecasted data. Holiday outliers or exceptional events may be removed from the set of historical data to prevent the estimation from deviating significantly. Conversely, forecasts for time periods including particular days such as holidays might be obtained by comparing the decrease and increase in demand for the holiday with other similar days (such as comparing Thanksgiving Day in the United States with other Thursdays in November and December, but excluding Thursdays which fall within two days of Christmas Day). Variations of this comparative analysis might be used to determine if other non-holiday dates throughout the year have abnormal demand and need to be separately factored.

The forecast may be presented to end users as in step 850 such as through use of a report or a user interface display. One example of outputs from the forecast may include expected order volumes per hour, or radiologist capacity available per hour. One further embodiment provides a scenario calendar to a user to allow easy selection of one or more future dates. This allows the data from the forecast to be selected or filtered for a range of dates. Another further embodiment may present user interface tools such as a calendar selector when establishing input of the historical and future data to the modeling engine, and generating a proposed schedule to address certain dates.

A variety of data presentation and selection features may be presented to users to enable additional customization of the forecasting and modeling. In one embodiment, these features include enabling user selection between a set of forecasts; displaying a short-term forecast as compared with actual demand for a period of time; and presenting a calendar or other proposed schedule having color-coded hours based on resource utilization. Further, the user interface may allow a user to enter a customized scenario (such as adding additional shifts for a radiologist during a set of time selected in a calendar) and running the forecast again to compare capacity.

In each of these embodiments, a plurality of sources for radiologist scheduling data may be queried and used as input in conjunction with the forecast and other scenarios. This may include a contracted schedule data source (e.g., a schedule defining radiologist shifts every Monday to Friday, 8 AM to 5 PM). Another schedule data source may provide common schedule customizations, such as time off, extra shifts, shift extensions, and the like. The final schedule which factors any forecast and the plurality of scheduling data sources is a "production" schedule that may be implemented into the radiology practice. The previously described scenario calendar may be used to test adjustments to a proposed schedule without affecting the production schedule. This aspect of the scenario calendar provides the ability to plan and experimenting with "what ifs" with actual radiologist scheduling scenarios.

The forecast generated by the modeling engine may also use extrapolation to divide its results into measurement units desired by business requirements or resource attributes. This may be helpful when estimating resource usage for resources who have some level of specialization, e.g., for radiologists with a specialty in neurology but are capable of performing more general types of reads.

The modeling engine functions may also operate to provide estimations in connection with future licensing, credentialing, certifications, specializations, or other related requirements for resources and resource consumers. For example, in connection with teleradiology, a radiologist must typically be credentialed or have been granted privileges by the medical facility who is requesting the radiology read. Additionally, other restrictions such as licensing by a state or federal entity in the jurisdiction of the medical facility must often be obtained as a prerequisite to credentialing.

In a typical radiology practice, obtaining credentials for additional radiologists at a medical facility might take 1-2 months. Obtaining licensing might take 1-3 months. Hiring additional skilled radiologists with certain subspeciality qualifications might take 6-9 months. The modeling engine factors these fact-based dependencies and requirements when providing forecasts and resource availability. Thus, the modeling engine may be configured to predict when a licensing approval is going to occur, followed by a credentialing approval, and predict when a radiologist will be fully available to begin conducting reads for a particular medical facility. The modeling engine may also suggest predictions to hire additional resources for a future period that is months in advance, or may factor a "what-if" scenario to determine if additional resources need to be hired if additional facilities are added or existing facilities increase usage over the next 3, 6, 9, or 12 or more months.

In further embodiments, predictions generated by the forecasting may be presented in an estimated range, as opposed to a single number or binary prediction. The estimated range may be compared to a statistical model to provide a degree of confidence for the prediction. For example, the model might present a 90% chance of falling between a range of 12-14 radiologists needed to handle estimated radiology read volume occurring in a 10 PM-2 AM period of time on a given date.

Additionally, as shown in step 860, a further embodiment may allow comparison of the forecast with actual resource usage to refine the algorithm and any data models used in connection with the forecast. For example, the speed of a given radiologist will vary from person-to-person and may increase over a period of time as the radiologist becomes more experienced or becomes more familiar with radiology imaging interfaces. The comparison of actual resource usage may also indicate that certain types of radiology read requests, such as neurology image requests, require far more time to analyze than x-ray images of limbs. Or, certain medical facilities may provide a larger number of images or more complex images that take more time to process and analyze as compared to other facilities.

Ultimately, the objective of the modeling engine is to produce the most accurate estimate of resource demand (i.e., radiology read requests) over a period of time such that the fewest number of resources (i.e., radiologists) can be scheduled and consumed. Therefore, numerous variations to the previously described embodiments may be implemented to match and predict resource usage to resource demand based on external constraints and factors.

Further, the presently described embodiments may be extended to factor availability for specific radiologists, scheduling preferences for the specific radiologists, and common scheduling scenarios such as one week on—one week off. As those skilled in the art would recognize, scheduling and future use of the prediction modeling described above may be implemented through a combination of automated computer-derived functions and manual input or human review. For example, a skilled manager with knowledge of scheduling and business-specific trends may review and adjust the final demand forecast and radiologist schedule before implementation in a radiology practice.

Use of an automated demand forecast and radiologist scheduling may require a set period of time and amount of input data to become more reliable. A radiology practice might choose to run the demand forecast in near-real time to monitor trends, or may choose to run the demand forecast at a less often interval such as once a week. Alternatively, a radiology practice may choose to compare a slightly modified "approved" forecast for an upcoming period of time and compare to the real-time schedule at regular intervals.

A variety of user interface embodiments may be used to interface with the previously described forecasting techniques. For example, graphs, charts, reports and other visual indicators may be presented to a user to allow a comparison of forecasting results with radiologist resource staffing levels and competencies. Ultimately, these indicators may be used by both skilled and unskilled users alike to speed up decision making, identify problem staffing levels, and proposing solutions to problem staffing levels. These indicators may be expressed in simple numerical or graphical data, or in more complex recommendations such as "Hire a neurology-skilled radiologist who is licensed in Florida to work on Thursdays" and "Switch Dr. X's shift with Dr. Y's shift next Wednesday."

Figure 9:
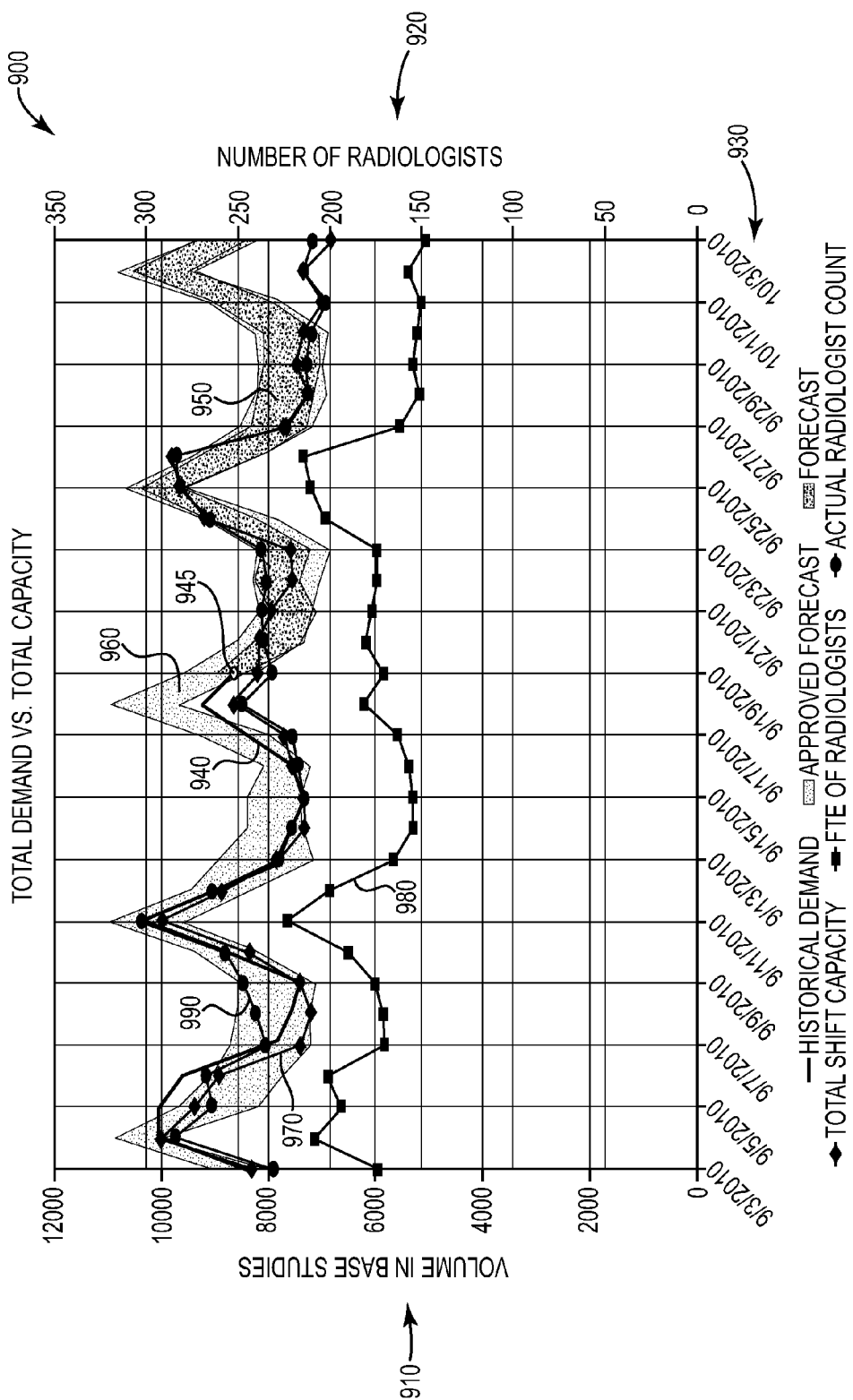
FIG. 9 is a graph illustrating an example set of data lines related to forecasting of radiology read demand and radiology read capacity.

For example, in one embodiment providing an example user interface, a graph presenting total radiology read request demand and total radiologist read capacity may be presented to users. FIG. 9 illustrates a graph 900 providing data volume of radiology studies 910 and number of radiologists 920 on a first axis graphed against daily time periods on a second axis 930. A number of data lines graphed among discrete data points are provided. In this example, the illustrated graph includes a historical demand data line 940 (graphed until the end of the available historical data on Sep. 11, 2010), a forward forecast range 950 which provides a range of values corresponding to a future demand forecast, and an approved forecast range 960 which provides a version of the forecast from a previous point in time which was approved for (for example, the forecast may be approved once a week, although the forward forecast may change from day-to-day). The approved forecast and forward forecast may be provided in a single data line in addition to or in lieu of a data range.

In addition to indications of historical and forecasted demand, a number of data lines are provided in the graph 900 to compare demand with actual and estimated radiologist capacity and radiologist staffing levels. These data lines include a total shift capacity data line 970 that provides an illustration of the capacity of all radiologists scheduled in each shift. The capacity of all radiologists corresponds to an indication of a radiologist full time equivalent (FTE) data line 980 which displays the number of projected radiologists equivalent to a full time radiologists working during each shift. An actual radiologist count data line 990 displays the number of projected radiologist persons working during each shift (which is generally higher than FTE because some of the radiologists may not work a full shift).

The graph displayed in FIG. 9 may be customized to display demand and capacity for an entire teleradiology practice comprising numerous radiologists and subscribing medical facilities. Alternately, this graph may be customized to display forecasts of demand and capacity on the basis of one or more criterion, such as the geographical state of the medical facility (recognizing that only certain radiologists licensed in that state may be available for radiology reads in that state); an individual medical facility (recognizing that only certain radiologists may be credentialed for radiology reads in the facility, and the facility may provide only certain types of radiology reads during certain times); a type of modality (recognizing that only certain radiologists may have expertise with certain modalities); a type of radiology subspeciality (recognizing that only certain radiologists may have subspeciality expertise); a type of radiology procedure (recognizing that radiologists may have expertise for or be unable to perform reads of images from certain procedures); and the like.

The data provided to the graph therefore may be customized to a specific type of radiology read request, for example, CT scans sent from Florida medical facilities. The capacity numbers displayed on such a graph would be updated to reflect radiologists who are scheduled during the time period that are qualified to read CTs in Florida. Radiologist and medical facility preferences may also be factored to exclude a radiologist from a certain procedure or medical facility.

In other embodiments, tools and other user interfaces may be used to analyze capacity and demand data to perform scheduling and radiologist matching to predicted and actual demand. For example, in one embodiment, a software tool may assign studies from expected demand to fill radiologist capacity, and show a user any shortfalls in coverage by state, medical facility, subspeciality, or procedure. In a more specific embodiment, summary level information related to radiologist usage may be provided hour-by-hour or day-by-day with statistics of study demand, study capacity, overage between demand and capacity, capacity minus demand, and capacity minus demand expressed as a percentage of capacity.

For example, as presented in the following Table 1, these values are provided hour-by-hour for two consecutive dates:

scheduling constraints in the forecasting model. One of the important business constraints for optimizing radiologist assignments in both the planning aspect and the workflow aspect is profitability. A goal of the forecasting data model is to maximize profit once standard of care and contractual obligations are met. To this end, the forecasting data model may also weigh radiologist cost and medical facility reimbursement as an important constraint when scheduling radiologists and estimating demand. For example, radiologist contractual quota information that is factored by the workflow module may also feed into the planning module, to provide additional metrics along with Capacity, Demand, Capacity-Demand, (C-D)/C, and Overage. In addition, the forecasting data model may also predict revenue based on estimated demand from each facility, and the contracted rates charged for each procedure expected to be received. This would allow the generation of "Revenue" and "Profit" metrics along with a "Cost" metric.

A number of embodiments of the invention have been described. Nevertheless, it will be understood that various modifications may be made without departing from the spirit and scope of the invention. For example, in some implementations, the medical request 108 includes an image, an order, or both. The images may include representations of body parts, such as x-rays, computed tomography (CT) scans, and magnetic resonance imaging (MRI) scans. The images may also contain additional information, such as Digital Information in Communications and Medicine (DICOM) data. For example, the additional information may include the number of images in the transmission, the name of the patient, a name of the medical facility 104 and a name of a device within the medical facility 104 where the image was created. In some implementations, the medical facility ID 110 comprises the name of the medical facility and the name of the device that are contained in the information associated with the image.

In other embodiments, the medical request may comprise information or images in a format other than DICOM format. For example, the medical request may comprise images in CTI ECAT 7 image format, which originated from CTI Molecular Imaging, Inc. of Knoxville, Tenn. A processor may extract the ECAT 7 data from image headers and store the information in the database 214. The processor may recognize the ECAT 7 file type by parsing the header and deter-

TABLE 1

|  |  | 9:00 PM | 10:00 PM | 11:00 PM | 12:00 AM | 1:00 AM | 2:00 AM | Total |
|---|---|---|---|---|---|---|---|---|
| Tuesday, September 14 | Overage | 2.69 | 8.22 | 15.34 | 67.58 | 103.81 | 68.71 | 266.35 |
|  | Demand | 531.76 | 612.00 | 690.00 | 700.00 | 690.00 | 593.00 | 3816.76 |
|  | Capacity | 559.10 | 607.61 | 675.18 | 632.42 | 586.19 | 524.29 | 3584.79 |
|  | Capacity – Demand | 27.34 | −4.39 | −14.82 | −67.58 | −103.81 | −68.71 | −231.97 |
|  | (C − D)/C | 4.89% | −0.72% | −2.20% | −10.69% | −17.71% | −13.11% | −6.47% |
| Wednesday, September 15 | Overage | 2.50 | 3.91 | 32.13 | 81.66 | 90.88 | 60.02 | 271.1 |
|  | Demand | 530.00 | 616.00 | 685.00 | 703.00 | 657.00 | 585.00 | 3776.00 |
|  | Capacity | 551.87 | 624.19 | 652.87 | 621.34 | 566.12 | 524.98 | 3541.37 |
|  | Capacity – Demand | 21.87 | 8.19 | −32.13 | −81.66 | −90.88 | −60.02 | −234.63 |
|  | (C − D)/C | 3.96% | 1.31% | −4.92% | −13.14% | −16.05% | −11.43% | −6.63% |

Other types and formats of reports may be generated. For example, simple reports may be generated to ignore capacity and demand ratios, and simply look for holes in coverage based on scheduled coverage of medical facilities. A color-coded chart of medical facilities may be generated to display a color indicator whether none, one, or more than two available radiologists are available to handle a radiology read from a specific modality type or procedure over a period of time.

In further embodiments, profit optimization constraints may be factored in addition to radiologist qualification and mining if a text string "MATRIX71" is at location 0 of the file. After the file is identified, information about the patient, such as name, age, and gender, may be extracted from the file along with additional information, such as the facility identifier.

The order may contain information about a patient, such as name, medical history, and the reason for creating the image. The order may also include a description of an associated image, such as a pelvic abdominal scan, a number of images associated with the order, and an order type, such as preliminary or final read. The presence of the patient name and other patient information may enable a particular image to be linked with a particular order.

For example, a patient may come into the medical facility 104 with an injury or sickness and one or more images may be taken of the patient. This image may be obtained by an image data source in the medical facility 104 or it may be transferred to the image data source from another image capturing device. The image data source, in turn, may transmit the image to a computing device that sends it over a network to the IO management system 102. The image data source may also directly send an image to the IO management system 102 instead of first transmitting it to the computing device. Medical facility personnel, such as a technician, may submit the order to a doctor or radiologist for reading the patient's images. The technician may enter the order into the computing device and send the order to the IO management system 102.

Medical facilities may send images and orders at the same time as one another or at different times. For example, in some implementations, the medical facility 104 sends the order before the images. In these implementations, the pre-populated order is not transmitted by the order server 204 to the medical facility 104, but the order is completed in full by personnel at the medical facility 104.

Images, orders, and reports may be sent over the same network or different networks. For example, the IO management system 102 may receive images and orders through a single T1 or T3 connection to the Internet, or the images may be received from the Internet through a T1 or T3 connection and the orders may be received through a modem connection. In another example, the IO management system 102 may receive an image and an order from a medical facility over the Internet and return a corresponding report to the medical facility over a fax connection.

Additionally, the images and orders may be sent separately or combined in one transmission. For instance, a computing device at a medical facility may use software that sends the orders and the images with a single application and single set of actions, or the medical facility may send the images using one application that sends one transmission and send the orders using a different application that sends a separate transmission.

The IO management system 102 may be implemented on a single computing device or on multiple computing devices, such as a server farm. In one implementation, the IO management system 102 may be disbursed over several servers that are connected through a network. This configuration may be advantageous by facilitating expansion of the system and flexibility in managing the flow of received and output images and orders.

Additionally, the doctor system may contain more than one computing device. For instance, there may be one computing device that accepts the images, decompresses them, and displays the images for the doctor. The other computing device may handle receiving the orders, displaying them to the doctor for acceptance, receiving the report from the doctor, and transmitting the report to the IO management system 102. The doctor may also not accept the order. For instance, if the doctor accessing the doctor system 106A is currently viewing an order previously received, the doctor may not be able to accept another order until the previous order is completed. In this situation, a different doctor may accept the order at another doctor system, such as the doctor system 106B. This is possible because the IO management system 102 may send the order to more than one doctor system. Once a doctor at one doctor system accepts an order, the IO management system 102 may remove the order from the other doctor systems.

The features of the present invention described herein may be implemented in digital electronic circuitry, or in computer hardware, firmware, software, or in combinations thereof. For example, a computer program product designed to perform functions of the described implementations may be embodied in one or more computer readable medium(s) having computer readable program code embodied thereon; an apparatus such as a computing system with a processor and memory may embody components structured to perform functions of the described implementations; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A program is generally a set of instructions that can be used, directly or indirectly, in a computer or other electronic programmable device to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

Although various representative embodiments of this invention have been described above with a certain degree of particularity, those skilled in the art could make numerous alterations to the disclosed embodiments without departing from the spirit or scope of the inventive subject matter set forth in the specification and claims.

What is claimed is:

1. A method for forecasting of medical resource assignments, comprising:
processing, with a computer system having at least one processor and memory, historical demand information obtained from a past set of electronic medical requests, the past set of electronic medical requests provided in a past period of time, and the past set of electronic medical requests requesting evaluation of one or more types of medical diagnostic imaging procedures performed across a set of medical facilities;
processing, with the computer system, future demand information for the one or more types of medical diagnostic imaging procedures expected in a future period of time;
forecasting, with the computer system, based on the historical demand information and the future demand information, a projected set of electronic medical requests expected to occur in the future period of time for the one or more types of medical diagnostic imaging procedures, the forecasting performed for a medical diagnostic imaging workflow that is configured to assign the projected set of electronic medical requests and projected data corresponding with the projected set of electronic medical requests to qualified medical resources in a set of medical resources; and
generating, with the computer system, a projected assignment of the projected set of electronic medical requests expected to occur in the medical diagnostic imaging workflow for the future period of time.

2. The method of claim 1, wherein generating a projected assignment of the projected set of electronic medical requests expected to occur in the medical diagnostic imaging workflow for the future period of time includes:
forecasting a timing and probability of one or more changes to the past set of electronic medical requests;
calculating an expected volume of the projected set of electronic medical requests expected to occur in the future period of time based on the forecasted timing and probability of one or more changes to the past set of electronic medical requests;
processing future availability information for the set of medical resources, the future availability information including information for changes to availability of the set of medical resources in the future period of time;
forecasting, based on the future availability information for the set of medical resources, probability and timing of the changes to availability of the set of medical resources; and
calculating expected medical resource availability for the future period of time by comparing the forecasted probability and timing of the changes to availability of the set of medical resources, with the expected volume of the projected set of electronic medical requests;
wherein the future period of time and the past period of time include at least one characteristic in common.

3. The method of claim 2, wherein the set of medical resources includes radiologists, the radiologists qualified to evaluate medical diagnostic images associated with the projected set of electronic medical requests on behalf of one or more of the set of medical facilities, wherein one or more parameters for a particular radiologist are matched to one or more parameters of a particular medical facility based on one or more parameters retrieved for the radiologists including: radiologist licensing information, radiologist credentialing information, radiologist subspecialty information, radiologist planned schedule information, radiologist preference information, or radiologist performance metric information.

4. The method of claim 3, further comprising:
implementing a schedule in the medical diagnostic imaging workflow based on the expected volume of the projected set of electronic medical requests and the expected medical resource availability for the future period of time.

5. The method of claim 3, further comprising:
comparing the expected volume of the projected set of electronic medical requests with the medical resource availability for the future period of time, to produce a prediction of a radiologist staffing level needed to fulfill the expected volume of the projected set of electronic medical requests.

6. The method of claim 5, wherein a prediction of any shortfall or excess in the prediction of the radiologist staffing level includes a range of values with an accompanying confidence level.

7. The method of claim 3, wherein the medical diagnostic imaging workflow is facilitated using a constraint provided from one or more of: radiologist specialty information, radiology procedure type information, radiologist credentialing information, radiologist licensing information, radiologist scheduling information, radiologist availability information, radiologist efficiency information, radiologist preference information, radiologist restriction information, medical facility preference information, medical facility restriction information, or medical facility location information.

8. The method of claim 1, wherein the qualified medical resources include radiologists, and wherein the historical demand information and future demand information includes information for one or more of: medical facility request volume, electronic medical request type, imaging modality information, medical facility preferences, radiologist preferences, radiologist efficiencies, coverage timing for respective medical facilities, contract timing for respective radiologists, expected licensing of the radiologists, or expected credentialing of the radiologists.

9. The method of claim 1, wherein the projected assignment of the projected set of electronic medical requests is generated for one or more subject medical facilities, and wherein the historical demand information is selected from one or more comparable medical facilities on the basis of one or more similar factors between the one or more comparable medical facilities and the one or more subject medical facilities, the similar factors including one or more of: size, geographic area, demographics, radiology procedure types, or radiology procedure volume.

10. The method of claim 1, wherein the projected assignment is performed for predicting any shortfall or excess in medical resource staffing levels based on a plurality of constraints related to matching selected radiologists to demand from selected medical facilities, the constraints including one or more of: radiologist specialty, radiology procedure type, radiologist credentialing, radiologist licensing, radiologist scheduling, radiologist availability, radiologist efficiency, radiologist preferences, radiologist restrictions, medical facility preferences, medical facility restrictions, or medical facility location.

11. The method of claim 1, wherein the projected assignment is performed for predicting any shortfall or excess in a radiologist staffing level for a new medical facility, wherein none of the historical data values are provided from the new medical facility.

12. The method of claim 1, wherein the projected set of electronic medical requests include radiology read requests and wherein the medical resources include radiologists, the method further comprising predicting an expected radiology read request volume per hour and an available radiologist read capacity per hour for the future period of time, wherein information relating to radiologist availability and radiologist read request volume included in the historical demand information and in the future demand information includes information aggregated into hourly chunks.

13. The method of claim 1, wherein outlier data from one or more holidays or other dates with an abnormal volume of the projected set of electronic medical requests is not considered from the historical demand information.

14. The method of claim 1, wherein forecasting based on the historical demand information and the future demand information includes an evaluation of one or more variances of the historical data values.

15. The method of claim 1, wherein the common characteristic includes one or more of: a common day of year, a common day of week, a common month, a common season, and a proximity to one or more common dates or holidays.

16. A system, comprising:
a data store configured to store electronic medical request data, the electronic medical request data including historical demand information obtained from historical electronic medical requests of respective past medical diagnostic imaging procedures conducted in a past period of time, and future demand information for forecasted medical diagnostic imaging procedures to occur in a future period of time; and
a forecasting system, including a processor and memory, configured to execute one or more instructions to generate forecasts, the one or more instructions configured for operation with the processor and the memory to perform operations to:
forecast a volume of projected electronic medical requests for the future period of time, the forecast of the volume of the projected electronic medical requests based on the historical demand information and the future demand information, and the forecast of the volume of electronic medical requests modified by changes to historical electronic medical requests expected by the future period of time;
forecast expected medical resource availability for the future period of time, the forecast of the expected medical resource availability produced from an evaluation of a forecasted probability and timing of the changes to medical resource availability, the expected medical resource availability forecasted for a medical diagnostic imaging workflow configured to assign the projected electronic medical requests and projected data corresponding with the projected electronic medical requests to particular qualified medical resources from a set of medical resources; and
forecast assignments and volume of the projected electronic medical requests to the particular qualified medical resources in the medical diagnostic imaging workflow for the future period of time.

17. The system of claim 16, wherein the particular qualified medical resources are radiologists, wherein the historical demand information and future demand information includes information for radiologist availability and radiology read request demand, including information for one or more of: medical facility request volumes, electronic medical request type, imaging modality information, medical facility preferences, radiologist preferences, radiologist efficiencies, coverage timing for respective medical facilities, contract timing for respective radiologists, expected licensing of the radiologists, or expected credentialing of the radiologists.

18. The system of claim 16, wherein the particular qualified medical resources are radiologists, and wherein the one or more instructions are further configured for operation with the processor and the memory to perform operations to:
forecast any shortfall or excess in a radiologist staffing level based on one or more constraints related to matching selected radiologists to demand from selected medical facilities, the one or more constraints including one or more of: radiologist specialty, radiology procedure type, radiologist credentialing, radiologist licensing, radiologist scheduling, radiologist availability, radiologist efficiency, radiologist preferences, radiologist restrictions, medical facility preferences, medical facility restrictions, or medical facility location.

19. A non-transitory machine-readable storage medium including instructions which when executed by a computing device cause the computing device to perform operations including:
processing historical demand information obtained from a past set of electronic medical requests, the past set of electronic medical requests correlated to respective past medical diagnostic imaging procedures occurring at medical facilities in a past period of time;
processing future demand information for future medical diagnostic imaging procedures expected to occur at the medical facilities in a future period of time, wherein the future period of time and the past period of time include a common characteristic;
processing future availability information for a group of medical resources qualified to evaluate the future medical diagnostic imaging procedures in the future period of time;
forecasting, based on the historical demand information and the future demand information from the past period of time, one or more changes to volume of the past set of electronic medical requests from the past period of time;
calculating an expected volume of a projected set of electronic medical requests expected to occur in the future period of time by modifying the historical demand information with the forecasted changes to volume of the past set of electronic medical requests;
forecasting, based on the future availability information, probability and timing of the changes to availability of the group of medical resources; and
calculating expected medical resource availability for the future period of time by factoring the forecasted probability and timing of the changes to availability, with the expected volume of the projected set of electronic medical requests.

20. The machine-readable storage medium of claim 19, wherein the group of medical resources include radiologists, and wherein the historical demand information and the future demand information relate to radiologist availability and radiology read request demand, and include information for one or more of: medical facility request volume, electronic medical request type, imaging modality information, medical facility preferences, radiologist preferences, radiologist efficiencies, coverage time for respective medical facilities, contract timing for respective radiologists, expected licensing of the radiologists, or expected credentialing of the radiologists.

21. The machine-readable storage medium of claim 19, wherein the group of medical resources include radiologists, and wherein the operations further include:

forecasting any shortfall or excess in radiologist staffing levels based on one or more constraints related to matching selected radiologists to demand from selected medical facilities, the one or more constraints including one or more of: radiologist specialty, radiology procedure type, radiologist credentialing, radiologist licensing, radiologist scheduling, radiologist availability, radiologist efficiency, radiologist preferences, radiologist restrictions, medical facility preferences, medical facility restrictions, or medical facility location.

* * * * *